United States Patent
Johnson et al.

(10) Patent No.: US 7,144,985 B2
(45) Date of Patent: Dec. 5, 2006

(54) METHODS AND REAGENTS FOR DIAGNOSIS AND TREATMENT OF DIABETES

(75) Inventors: Jeffrey D. Johnson, Moraga, CA (US); John E. Blume, Danville, CA (US); John F. Palma, San Ramon, CA (US); Yun-Ping Zhou, San Ramon, CA (US)

(73) Assignee: Metabolex, Inc., Hayward, CA (US)

( * ) Notice: Subject to any disclaimer, the term of this patent is extended or adjusted under 35 U.S.C. 154(b) by 413 days.

(21) Appl. No.: 10/308,393

(22) Filed: Dec. 2, 2002

(65) Prior Publication Data

US 2003/0202976 A1 Oct. 30, 2003

Related U.S. Application Data

(60) Provisional application No. 60/336,633, filed on Dec. 3, 2001.

(51) Int. Cl.
*C07K 4/12* (2006.01)
*C07K 16/18* (2006.01)
*A16K 38/01* (2006.01)
*A16K 38/28* (2006.01)
*C12N 5/08* (2006.01)
*G01N 33/48* (2006.01)
*C12P 21/06* (2006.01)

(52) U.S. Cl. .................. 530/350; 514/12; 514/435; 514/7.1; 514/3; 514/320.1; 435/325; 435/69.1; 424/146.1; 424/23.5; 530/388

(58) Field of Classification Search ............... 435/4, 435/325, 7.1, 69.1, 320.1, 23.5; 530/350, 530/388; 514/12, 3; 424/146.1
See application file for complete search history.

(56) References Cited

U.S. PATENT DOCUMENTS

2002/0082409 A1 6/2002 Hsu et al.
2003/0036507 A1 2/2003 Vale et al.

FOREIGN PATENT DOCUMENTS

WO WO 02/34934 A2 5/2002
WO WO 02/74326 A2 9/2002

OTHER PUBLICATIONS

Lewis et al. GenBank Accession No. AAK67317, "*Homo sapiens* urocortin III (UCNIII) gene, complete cds", Jun. 27, 2001.*
Hsu et al., *Nature Medicine*, 7:5: 605-611 (2001).
Lewis et al., *PNAS*, 98:13: 7570-7575 (2001).
Barroso et al., *Nature* 23/30:402: 880-883 (1999).
Hu et al., *Science* 274: 2100-2103 (1996).

* cited by examiner

*Primary Examiner*—Ponnathapu Achutamurthy
*Assistant Examiner*—Iqbal Chowdhury
(74) *Attorney, Agent, or Firm*—Townsend and Townsend and Crew LLP

(57) ABSTRACT

The invention relates to methods of determining islet cell activity by detecting the level of Archipelin or a fragment thereof and comparing the level to a baseline level or range associated with a known islet cell activity. Such methods are useful in diagnosing and studying the development of diabetes.

10 Claims, 8 Drawing Sheets

Figure 3

Corticotropin-releasing factor family signature

| Protein | Species | Sequence |
|---|---|---|
| | | X S F S V N P A V D I L Q H R Y M E K V A Q N N R N F L N R V X |
| DIURETIC HORMONE 2 | tobacco hornworm | Q S L S I V A P L D V L R Q R L L N E L A R R R M R E L Q G S R |
| DIURETIC HORMONE | house cricket | P P I S I D L S L E L L R K M I E I E K Q E K Q Q A A N N R |
| SAUVAGINE | sauvage's leaf frog | P P S L D L T F H L L R E V L E M A R A E Q L A Q Q A H S N R |
| CORTICOLIBERIN 1 PRECURSOR | white sucker | P P I S L D L T F H L L R E V L E M A R A E Q L V Q Q A H S N R |
| CORTICOLIBERIN 2 PRECURSOR | white sucker | P P I S L D L T F H L L R E V L E M A R A E Q L A Q Q A H S N R |
| CORTICOLIBERIN PRECURSOR | human | P P I S L D L T F H L L R E V L E M A R A E Q L A Q Q A H S N R |
| CORTICOLIBERIN PRECURSOR | pig | P P I S L D L T F H L L R E V L E M A R A E Q L A Q Q A H S N R |
| CORTICOLIBERIN PRECURSOR | rat | P P I S L D L T F H L L R E V L E M T K A D Q L A Q Q A H S N R |
| CORTICOLIBERIN PRECURSOR | sheep | P P I S L D L T F H L L R E V L E M A R A E Q I A R R R L R D A E E Q I |
| CORTICOLIBERIN PRECURSOR | xenopus | P S L S I V N P M D V L R Q R L L L E I A R R Q M K E N T R Q V |
| DIURETIC HORMONE | locust | P S L S I V N P L D V L R Q R L L L E L A R R R M R Q S Q D Q I |
| DIURETIC HORMONE | stable fly | P P I S L D L T F H L L R N M I E M A R I E N E R E Q A G L N R |
| DIURETIC HORMONE | cockroach | P S L S I D L T F H L L R N M I E M A R N E N Q R E Q A G L N R |
| UROTENSIN I | white sucker | P P L S I D L T F H L L R T L L E L A R T Q S Q R E R A E Q N R |
| UROTENSIN I PRECURSOR | common carp | P P L S I D L T F H L L R T L L E L A R T Q S Q R E R A E Q N R |
| UROCORTIN PRECURSOR | human | L T L S L D V P T N I M N I L F D V A K A K N L R A A E N A A |
| UROCORTIN PRECURSOR | rat | F T L S L D V P T N I M N L L F N I A K A K N L R A A A N A |
| UROCORTIN PRECURSOR | mouse | F T L S L D V P T N I M N I L F N I D K A K N L R A K A A N A |
| UROCORTIN PRECURSOR | pufferfish | F T L S L D V P T N I M N I L F N I D K A K N L R A K A A A N A |
| Metabolex Archipelin | human | | 
| Metabolex Archipelin | rat | |
| Metabolex Archipelin | mouse | |
| Corticotropin-releasing factor family signature | | |

Figure 4

Human Archipelin N-terminal proteolytic cleavage sites and the C-terminal cleavage site N-terminal cleavage sites are marked with a |. The C-terminal cleavage site is marked with a !

MLMPVHFLLLLLLLGGPRTGLPHKFYKAKPIFSCLNTALSEAEKGQWEDASLLSKRSFHYLRSRDASSGEEEGKEK
KTFPISGARGGARGTRYRYVSQAQPR|GK|PR|QDTAK|SPHR|TK|FTLSLDVPTNMNLLFNIAKAKNLRAQAAANAHL
MAQIG!RKK

The following are mature human Archipelin peptides:

FTLSLDVPTNMNLLFNIAKAKNLRAQAAANAHLMAQI-CONH2

TKFTLSLDVPTNMNLLFNIAKAKNLRAQAAANAHLMAQI-CONH2

SPHRTKFTLSLDVPTNMNLLFNIAKAKNLRAQAAANAHLMAQI-CONH2

QDTAKSPHRTKFTLSLDVPTNMNLLFNIAKAKNLRAQAAANAHLMAQI-CONH2

PRQDTAKSPHRTKFTLSLDVPTNMNLLFNIAKAKNLRAQAAANAHLMAQI-CONH2

GKPRQDTAKSPHRTKFTLSLDVPTNMNLLFNIAKAKNLRAQAAANAHLMAQI-CONH2

-CONH2 indicates that the C-terminal residue is isoleucyl-amide

At residue 91 (underlined), there is a coding variant. Multiple clones show a clear arg (R) at this position and multiple clones show a clear gly (G) at this position due to a one nucleotide variation.

Figure 5

Mouse Archipelin N-terminal proteolytic cleavage sites and the C-terminal cleavage site N-terminal cleavage sites are marked with a |. The C-terminal cleavage site is marked with a !

MLMPTYFLLPLLLLGGPRTSLSHKFYNTGPVFSCLNTALSEVKKNKLEDVPLLSKKSFGHLPTQDPSGEEDNQTHLQIK
RTFSGAAGGNGAGSTRYRYQSQAQHKGK|LYPDK|PK|SDR|GTKFTLSLDVPTNIMNILFNIDKAKNLRAKAAANAQLMA
QIG!KKK

The predicted mouse Archipelin mature peptides are:

TKFTLSLDVPTNIMNILFNIDKAKNLRAKAAANAQLMAQI-CONH2

GTKFTLSLDVPTNIMNILFNIDKAKNLRAKAAANAQLMAQI-CONH2

SDRGTKFTLSLDVPTNIMNILFNIDKAKNLRAKAAANAQLMAQI-CONH2

PKSDRGTKFTLSLDVPTNIMNILFNIDKAKNLRAKAAANAQLMAQI-CONH2

LYPDKPKSDRGTKFTLSLDVPTNIMNILFNIDKAKNLRAKAAANAQLM
AQI-CONH2

The —CONH2 indicates that the C-terminal residue is an isoleucyl-amide.

Figure 6

Rat Archipelin N-terminal proteolytic cleavage sites and the C-terminal cleavage site N-terminal cleavage sites are marked with a |. The C-terminal cleavage site is marked with a !

MLMPTYFLLLLLLLGGPRTSLSHKFYNAGPIFSCLNTALSEVKKNKLEDVPVLSKKNFGYLPTQDPSGEEEDEQKHIKN
KRTFSDAVGGNGGRSIRYRYQSPAQPK|GK|LYPDK|VK|NDR|GTKFTLSLDVPTNIMNILFNIDKAKNLRAKAAANAQL
MAQIG!KKK

The mature rat Archipelin peptide sequences are:

TKFTLSLDVPTNIMNILFNIDKAKNLRAKAAANAQLMAQI-CONH2

GTKFTLSLDVPTNIMNILFNIDKAKNLRAKAAANAQLMAQI-CONH2

NDRGTKFTLSLDVPTNIMNILFNIDKAKNLRAKAAANAQLMAQI-CONH2

VKNDRGTKFTLSLDVPTNIMNILFNIDKAKNLRAKAAANAQLMAQI-CONH2

LYPDKVKNDRGTKFTLSLDVPTNIMNILFNIDKAKNLRAKAAANAQLMAQI-CONH2

GKLYPDKVKNDRGTKFTLSLDVPTNIMNILFNIDKAKNLRAKAAANAQLMAQI-CONH2

-CONH2 indicates that the C-terminal residue is a isoleucyl-amide.

United States Patent US 7,144,985 B2

METHODS AND REAGENTS FOR DIAGNOSIS AND TREATMENT OF DIABETES

CROSS REFERENCE TO RELATED APPLICATIONS

This application claims priority to U.S. Provisional Patent Application No. 60/336,633, filed on Dec. 3, 2001, which is incorporated by reference in its entirety.

FIELD OF THE INVENTION

This invention relates to methods and reagents useful for treatment and diagnosis of diabetes.

BACKGROUND OF THE INVENTION

Diabetes mellitus can be divided into two clinical syndromes, Type 1 and Type 2 diabetes mellitus. Type 1, or insulin-dependent diabetes mellitus (IDDM), is a chronic autoimmune disease characterized by the extensive loss of beta cells in the pancreatic Islets of Langerhans (hereinafter referred to as "pancreatic islet cells" or "islet cells"), which produce insulin. As these cells are progressively destroyed, the amount of secreted insulin decreases, eventually leading to hyperglycemia (abnormally high level of glucose in the blood) when the amount secreted drops below the level required for euglycemia (normal blood glucose level). Although the exact trigger for this immune response is not known, patients with IDDM have high levels of antibodies against pancreatic beta cells. However, not all patients with high levels of these antibodies develop IDDM.

Type 2 diabetes develops when muscle, fat and liver cells fail to respond normally to insulin. This failure to respond (called insulin resistance) may be due to reduced numbers of insulin receptors on these cells, or a dysfunction of signaling pathways within the cells, or both. The beta cells initially compensate for this insulin resistance by increasing their insulin output. Over time, these cells become unable to produce enough insulin to maintain normal glucose levels, indicating progression to type 2 diabetes.

Type 2 diabetes is brought on by a combination of poorly understood genetic and acquired risk factors—including a high-fat diet, lack of exercise, and aging. Worldwide, type 2 diabetes has become an epidemic, driven by increases in obesity and a sedentary lifestyle, widespread adoption of western dietary habits, and the general aging of the populations in many countries. In 1985, an estimated 30 million people worldwide had diabetes—by 2000, this figure had increased 5-fold, to an estimated 154 million people. The number of people with diabetes is expected double between now and 2025, to about 300 million.

There is no cure for diabetes. Conventional treatments for diabetes are very limited, and focus on attempting to control blood glucose levels in order to minimize or delay complications. The present invention addresses these and other problems.

BRIEF SUMMARY OF THE INVENTION

This invention provides isolated nucleic acids encoding an Archipelin polypeptide. In some embodiments, the Archipelin polypeptide is at least 60% identical to SEQ ID NO:2. In some embodiments, the nucleic acid encodes SEQ ID NO:2. In some embodiments, wherein the nucleic acid comprises SEQ ID NO:1. In some embodiments, the nucleic acid encodes SEQ ID NO:7. In some embodiments, the nucleic acid comprises SEQ ID NO:8. In some embodiments, the nucleic acid encodes SEQ ID NO:6. In some embodiments, the nucleic acid comprises SEQ ID NO:5. In some embodiments, the polypeptide comprises an amino acid sequence selected from the group consisting of SEQ ID NO:9, SEQ ID NO:10, SEQ ID NO:11, SEQ ID NO:12, SEQ ID NO:13, and SEQ ID NO:14. In some embodiments, the nucleic acid is amplified by a primer set selected from the group consisting of GCGATGTTGAAGAAGAAGTTC (SEQ ID NO:15) and ATCGCCAAGGCCAAGA (SEQ ID NO:16).

The present invention also provides expression cassettes comprising a promoter operably linked to a nucleic acid encoding an polypeptide at least 605 identical to SEQ ID NO:9.

The present invention also provides isolated nucleic acids that specifically hybridizes following at least one wash in 0.2×SSC at 55° C. for 20 minutes to a probe comprising SEQ ID NO:1.

The present invention also provides isolated polypeptides comprising an amino acid sequence at least 60% identical to SEQ ID NO:9. In some embodiments, the polypeptide comprises an amino acid sequence selected from the group consisting of SEQ ID NO:9, SEQ ID NO:10, SEQ ID NO:11, SEQ ID NO:12, SEQ ID NO:13, and SEQ ID NO:14. In some embodiments, the polypeptide comprises SEQ ID NO:2. In some embodiments, the polypeptide comprises SEQ ID NO:6. In some embodiments, the polypeptide specifically binds to antibodies generated against SEQ ID NO:9.

The present invention also provides antibodies that specifically hybridizes to Archipelin polypeptides. In some embodiments, polypeptides comprising an amino acid sequence at least 60% identical to SEQ ID NO:9.

The present invention also provides host cells transfected with a nucleic acid encoding an polypeptide at least 60% identical to SEQ ID NO:9. In some embodiments, the cell is a pancreatic islet cell.

The present invention also provides pharmaceutical compositions comprising insulin and a polypeptide at least 60% identical to SEQ ID NO:9. In some embodiments, the polypeptide comprises an amino acid sequence selected from the group consisting of SEQ ID NO:9, SEQ ID NO:10, SEQ ID NO:11, SEQ ID NO:12, SEQ ID NO:13, and SEQ ID NO:14. In some embodiments, the polypeptide comprises SEQ ID NO:2. In some embodiments, the pharmaceutical composition is suitable for injection.

The present invention also provides methods of diagnosing type 1 or type 2 diabetes or a predisposition for type 1 or type 2 diabetes in a patient. In some embodiments, the methods comprise detecting the level of a polypeptide at least 60% identical to SEQ ID NO:9 in a sample from the patient, wherein a modulated level of the polypeptide in the sample compared to a level of the polypeptide in a non-diabetic individual indicates that the patient is diabetic or is predisposed for at least some pathological aspects of diabetes. In some embodiments, the modulated level of the polypeptide in the sample is lower than a level of the polypeptide in a non-diabetic individual. In some embodiments, the modulated level of the polypeptide in the sample is higher than a level of the polypeptide in a non-diabetic individual. In some embodiments, the polypeptide comprises an amino acid sequence selected from the group consisting of SEQ ID NO:9, SEQ ID NO:10, SEQ ID NO:11, SEQ ID NO:12, SEQ ID NO:13, and SEQ ID NO:14. In some embodiments, the polypeptide comprises SEQ ID NO:2. In some embodiments, the polypeptide is detected by an antibody. In some embodiments, the level of the polypeptide in the patient is less than 50% of the level from the non-diabetic individual. In some embodiments, the level of the polypeptide in the patient is at least 150% of the level from the non-diabetic individual.

The present invention also provides methods of treating a patient diagnosed with type 1 or type 2 diabetes. In some embodiments, the method comprise administering to the patient a pharmaceutical composition comprising a therapeutically effective amount of a compound selected from the group consisting of an agonist of Archipelin and an agent that increases expression of Archipelin. In some embodiments, the compound is an agonist of Archipelin. In some embodiments, the compound is an agent that increases expression of Archipelin. In some embodiments, the agonist is a polypeptide at least 60% identical to SEQ ID NO:9. In some embodiments, the agonist comprises a polypeptide comprising SEQ ID NO:2. In some embodiments, the polypeptide comprises an amino acid sequence selected from the group consisting of SEQ ID NO:9, SEQ ID NO:10, SEQ ID NO:11, SEQ ID NO:12, SEQ ID NO:13, and SEQ ID NO:14. In some embodiments, the pharmaceutical composition comprises insulin. In some embodiments, the pharmaceutical composition is administered parenterally. In some embodiments, the pharmaceutical composition is administered by injection. In some embodiments, the pharmaceutical composition is administered by a pump device.

The present invention also provides methods of modulating Archipelin activity in a cell. In some embodiments, the methods comprise introducing into a pancreatic islet cell an expression cassette comprising a promoter operably linked to a polynucleotide encoding a polypeptide at least 60% identical to SEQ ID NO:9. In some embodiments, the polypeptide comprises SEQ ID NO:2. In some embodiments, the polypeptide comprises an amino acid sequence selected from the group consisting of SEQ ID NO:9, SEQ ID NO:10, SEQ ID NO:11, SEQ ID NO:12, SEQ ID NO:13, and SEQ ID NO:14. In some embodiments, the cell is introduced into a patient. In some embodiments, the cell is from the patient. In some embodiments, the expression cassette is contained in a viral vector.

The present invention also provides methods of identifying an agent useful for the treatment of diabetes. In some embodiments, the methods comprise contacting a cell with an agent; and selecting an agent that modulates the expression in the cell of a polypeptide at least 60% identical to SEQ ID NO:9. In some embodiments, the polypeptide comprises an amino acid sequence selected from the group consisting of SEQ ID NO:9, SEQ ID NO:10, SEQ ID NO:11, SEQ ID NO:12, SEQ ID NO:13, and SEQ ID NO:14. In some embodiments, the cell is from a diabetic animal. In some embodiments, the diabetic animal is a human. In some embodiments, the cell is a pancreatic islet cell. In some embodiments, the polypeptide comprises SEQ ID NO:2. In some embodiments, the expression of the polypeptide is increased following the contacting step.

The present invention also provides methods of treating a patient diagnosed with type 1 or type 2 diabetes. In some embodiments, the methods comprise administering a therapeutically effective amount of an agent which was identified by contacting a cell with an agent; and selecting an agent that modulates the expression in the cell of a polypeptide at least 60% identical to SEQ ID NO:9. In some embodiments, the agent increases the expression of the polypeptide in the patient.

DEFINITIONS

"Antibody" refers to a polypeptide substantially encoded by an immunoglobulin gene or immunoglobulin genes, or fragments thereof which specifically bind and recognize an analyte (antigen). The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kD) and one "heavy" chain (about 50–70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially an Fab with part of the hinge region (see, Paul (Ed.) *Fundamental Immunology*, Third Edition, Raven Press, NY (1993)). While various antibody fragments are defined in terms of the digestion of an intact antibody, one of skill will appreciate that such fragments may be synthesized de novo either chemically or by utilizing recombinant DNA methodology. Thus, the term antibody, as used herein, also includes antibody fragments either produced by the modification of whole antibodies or those synthesized de novo using recombinant DNA methodologies (e.g., single chain Fv).

The terms "peptidomimetic" and "mimetic" refer to a synthetic chemical compound that has substantially the same structural and functional characteristics of the Archipelin polypeptides of the invention. Peptide analogs are commonly used in the pharmaceutical industry as non-peptide drugs with properties analogous to those of the template peptide. These types of non-peptide compound are termed "peptide mimetics" or "peptidomimetics" (Fauchere, J. *Adv. Drug Res.* 15:29 (1986); Veber and Freidinger *TINS* p. 392 (1985); and Evans et al. *J. Med. Chem.* 30:1229 (1987), which are incorporated herein by reference). Peptide mimetics that are structurally similar to therapeutically useful peptides may be used to produce an equivalent or enhanced therapeutic or prophylactic effect. Generally, peptidomimetics are structurally similar to a paradigm polypeptide (i.e., a polypeptide that has a biological or pharmacological activity), such as found in Archipelin, but have one or more peptide linkages optionally replaced by a linkage selected from the group consisting of, e.g., —CH2NH—, —CH2S—, —CH2-CH2-, —CH=CH— (cis and trans), —COCH2-, —CH(OH)CH2-, and —CH2SO—. The mimetic can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity. For example, a mimetic composition is within the scope of the invention if it is capable of carrying out the binding or enzymatic activities of Archipelin.

The term "gene" means the segment of DNA involved in producing a polypeptide chain; it includes regions preceding and following the coding region (leader and trailer) as well as intervening sequences (introns) between individual coding segments (exons).

The term "isolated," when applied to a nucleic acid or protein, denotes that the nucleic acid or protein is essentially free of other cellular components with which it is associated in the natural state. It is preferably in a homogeneous state although it can be in either a dry or aqueous solution. Purity and homogeneity are typically determined using analytical chemistry techniques such as polyacrylamide gel electrophoresis or high performance liquid chromatography. A protein which is the predominant species present in a preparation is substantially purified. In particular, an isolated gene is separated from open reading frames which flank the gene and encode a protein other than the gene of interest. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

The term "nucleic acid" refers to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605–2608 (1985); and Cassol et al. (1992); Rossolini et al., *Mol. Cell. Probes* 8:91–98 (1994)). The term nucleic acid is used interchangeably with gene, cDNA, and mRNA encoded by a gene.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full length proteins (i.e., antigens), wherein the amino acid residues are linked by covalent peptide bonds.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

An "Archipelin nucleic acid" or "Archipelin polynucleotide sequence" of the invention is a subsequence or full-length polynucleotide sequence of a gene that encodes a polypeptide expressed in pancreatic islet cells. Exemplary Archipelin nucleic acids of the invention include sequences substantially identical to SEQ ID NO:1, SEQ ID NO:3, SEQ ID NO:5, and SEQ ID NO:8. Similarly, "Archipelin polypeptide" or "Archipelin" refers to a polypeptide, or fragment thereof, that is substantially identical to a polypeptide encoded by SEQ ID NO:1, SEQ ID NO:3, SEQ ID NO:5, and SEQ ID NO:8 (e.g., SEQ ID NO:2, SEQ ID NO:4, SEQ ID NO:6, SEQ ID NO:7, and SEQ ID NOs: 9–14) or peptidomimetic compositions with substantially the same activity as SEQ ID NO:2, SEQ ID NO:4, SEQ ID NO:6, SEQ ID NO:7, and SEQ ID NOs:9–14.

"Conservatively modified variants" applies to both amino acid and nucleic acid sequences. With respect to particular nucleic acid sequences, "conservatively modified variants" refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, Proteins (1984)).

Macromolecular structures such as polypeptide structures can be described in terms of various levels of organization. For a general discussion of this organization, see, e.g., Alberts et al., *Molecular Biology of the Cell* (3$^{rd}$ ed., 1994) and Cantor and Schimmel, *Biophysical Chemistry Part I. The Conformation of Biological Macromolecules* (1980). "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically 50 to 350 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, optionally 65%, 70%, 75%, 80%, 85%, 90%, or 95% identity over a specified region), when compared and aligned for maximum correspondence over a comparison window, or designated region as measured using one of the following sequence comparison algorithms or by manual alignment and visual inspection. Such sequences are then said to be "substantially identical." This definition also refers to the complement of a test sequence. Optionally, the identity exists over a region that is at least about 50 amino acids or nucleotides in length, or more preferably over a region that is 75–100 amino acids or nucleotides in length.

The term "similarity," or percent "similarity," in the context of two or more polypeptide sequences, refer to two or more sequences or subsequences that have a specified percentage of amino acid residues that are either the same or similar as defined in the 8 conservative amino acid substitutions defined above (i.e., 60%, optionally 65%, 70%, 75%, 80%, 85%, 90%, or 95% similar over a specified region), when compared and aligned for maximum correspondence over a comparison window, or designated region as measured using one of the following sequence comparison algorithms or by manual alignment and visual inspection. Such sequences are then said to be "substantially similar." Optionally, this identity exists over a region that is at least about 50 amino acids in length, or more preferably over a region that is at least about 75–100 amino acids in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith and Waterman (1970) *Adv. Appl. Math.* 2:482c, by the homology alignment algorithm of Needleman and Wunsch (1970) *J. Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng and Doolittle (1987) *J. Mol. Evol.* 35:351–360. The method used is similar to the method described by Higgins and Sharp (1989) *CABIOS* 5:151–153. The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al. (1984) *Nuc. Acids Res.* 12:387–395).

Another example of algorithm that is suitable for determining percent sequence identity and sequence similarity are the BLAST and BLAST 2.0 algorithms, which are described in Altschul et al. (1977) *Nuc. Acids Res.* 25:3389–3402, and Altschul et al. (1990) *J. Mol. Biol.* 215:403–410, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci. USA* 90:5873–5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below.

Yet another indication that two nucleic acid sequences are substantially identical is that the same primers can be used to amplify the sequence.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5–10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, optionally 10 times background hybridization. Exemplary stringent hybridization conditions can be as following: 50% formamide, 5×SSC, and 1% SDS, incubating at 42° C., or 5×SSC, 1% SDS, incubating at 65° C., with wash in 0.2×SSC, and 0.1% SDS at 65° C. Such washes can be performed for 5, 15, 30, 60, 120, or more minutes.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. Such washes can be performed for 5, 15, 30, 60, 120, or more minutes. A positive hybridization is at least twice background. Those of ordinary skill will readily recognize that alternative hybridization and wash conditions can be utilized to provide conditions of similar stringency.

The phrase "a nucleic acid sequence encoding" refers to a nucleic acid which contains sequence information for a structural RNA such as rRNA, a tRNA, or the primary amino acid sequence of a specific protein or peptide, or a binding site for a trans-acting regulatory agent. This phrase specifically encompasses degenerate codons (i.e., different codons which encode a single amino acid) of the native sequence or sequences which may be introduced to conform with codon preference in a specific host cell.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (nonrecombinant) form of the cell or express native genes that are otherwise abnormally expressed, under-expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The phrase "specifically (or selectively) binds to an antibody" or "specifically (or selectively) immunoreactive with", when referring to a protein or peptide, refers to a binding reaction which is determinative of the presence of the protein in the presence of a heterogeneous population of proteins and other biologics. Thus, under designated immunoassay conditions, the specified antibodies bind to a particular protein and do not bind in a significant amount to other proteins present in the sample. Specific binding to an antibody under such conditions may require an antibody that is selected for its specificity for a particular protein. For example, antibodies raised against a protein having an amino acid sequence encoded by any of the polynucleotides of the invention can be selected to obtain antibodies specifically immunoreactive with that protein and not with other proteins, except for polymorphic variants. A variety of immunoassay formats may be used to select antibodies specifically immunoreactive with a particular protein. For example, solid-phase ELISA immunoassays, Western blots, or immunohistochemistry are routinely used to select monoclonal antibodies specifically immunoreactive with a protein. See, Harlow and Lane *Antibodies, A Laboratory Manual*, Cold Spring Harbor Publications, NY (1988) for a description of immunoassay formats and conditions that can be used to determine specific immunoreactivity. Typically, a specific or selective reaction will be at least twice the background signal or noise and more typically more than 10 to 100 times background.

"Inhibitors," "activators," and "modulators" of Archipelin expression or of Archipelin activity are used to refer to inhibitory, activating, or modulating molecules, respectively, identified using in vitro and in vivo assays for Archipelin expression or Archipelin signaling, e.g., ligands, agonists, antagonists, and their homologs and mimetics. Modulators include inhibitors and activators. Inhibitors are compounds that, e.g., inhibit expression of Archipelin or bind to, partially or totally block stimulation, decrease, prevent, delay activation, inactivate, desensitize, or down regulate the activity of Archipelin or that bind or down regulate a receptor to which Archipelin binds. e.g., antagonists. Activators are compounds that, e.g., induce or activate the expression of a Archipelin or bind to, stimulate, increase, open, activate, facilitate, enhance activation, sensitize or up regulate the activity of Archipelin or that bind or up regulate a receptor to which Archipelin binds, e.g., agonists. Modulators include compounds that, e.g., alter the interaction of Archipelin with: extracellular proteins that bind activators or inhibitors, receptors, including G-proteins coupled-receptors (GPCRs), kinases, etc. Modulators include genetically modified versions of Archipelin, e.g., with altered activity, as well as naturally occurring and synthetic ligands, antagonists, agonists, small chemical molecules and the like. Such assays for inhibitors and activators include, e.g., applying putative modulator compounds to pancreatic islet cells, in the presence or absence of Archipelin and then determining the functional effects on Archipelin signaling, as described above. Samples or assays comprising Archipelin that are treated with a potential activator, inhibitor, or modulator are compared to control samples without the inhibitor, activator, or modulator to examine the extent of inhibition. Control samples (untreated with inhibitors) are assigned a relative Archipelin activity value of 100%. Inhibition of a Archipelin is achieved when the Archipelin activity value relative to the control is less than about 80%, optionally less than about 50% or less than about 25–0%. Activation of a Archipelin is achieved when the Archipelin activity value relative to the control is at least about 110%, optionally at least about 150%, optionally at least about 200–500%, or at least about 1000–3000% or higher.

BRIEF DESCRIPTION OF THE DRAWINGS

FIG. 3 illustrates an amino acid alignment of Archipelin sequences (SEQ ID NOS:33 and 34) compared to peptides from the CRF peptide family (SEQ ID NOS:17–32).

FIG. 4 illustrates potential amino-terminal and carboxyl-terminal cleavage sites of the human Archipelin proprotein (SEQ ID NO:2). Potential amino terminal cleavage sites are marked with a "/". Potential carboxyl terminal cleavage sites are marked with a "!". Mature human Archipelin peptides=SEQ ID NOS:35–40.

FIG. 5 illustrates potential amino-terminal and carboxyl-terminal cleavage sites of the mouse Archipelin proprotein (SEQ ID NO:4). Potential amino terminal cleavage sites are marked with a "/". Potential carboxyl terminal cleavage sites are marked with a "!". Mature mouse Archipelin peptides=SEQ ID NOS:41–45.

FIG. 6 illustrates potential amino-terminal and carboxyl-terminal cleavage sites of the rat Archipelin proprotein (SEQ ID NO:6). Potential amino terminal cleavage sites are marked with a "/". Potential carboxyl terminal cleavage sites are marked with a "!". Mature rat Archipelin peptides=SEQ ID NOS:41, 42, 46, 47, 45 and 48, respectively.

DETAILED DESCRIPTION

I. Introduction

Figure 1:
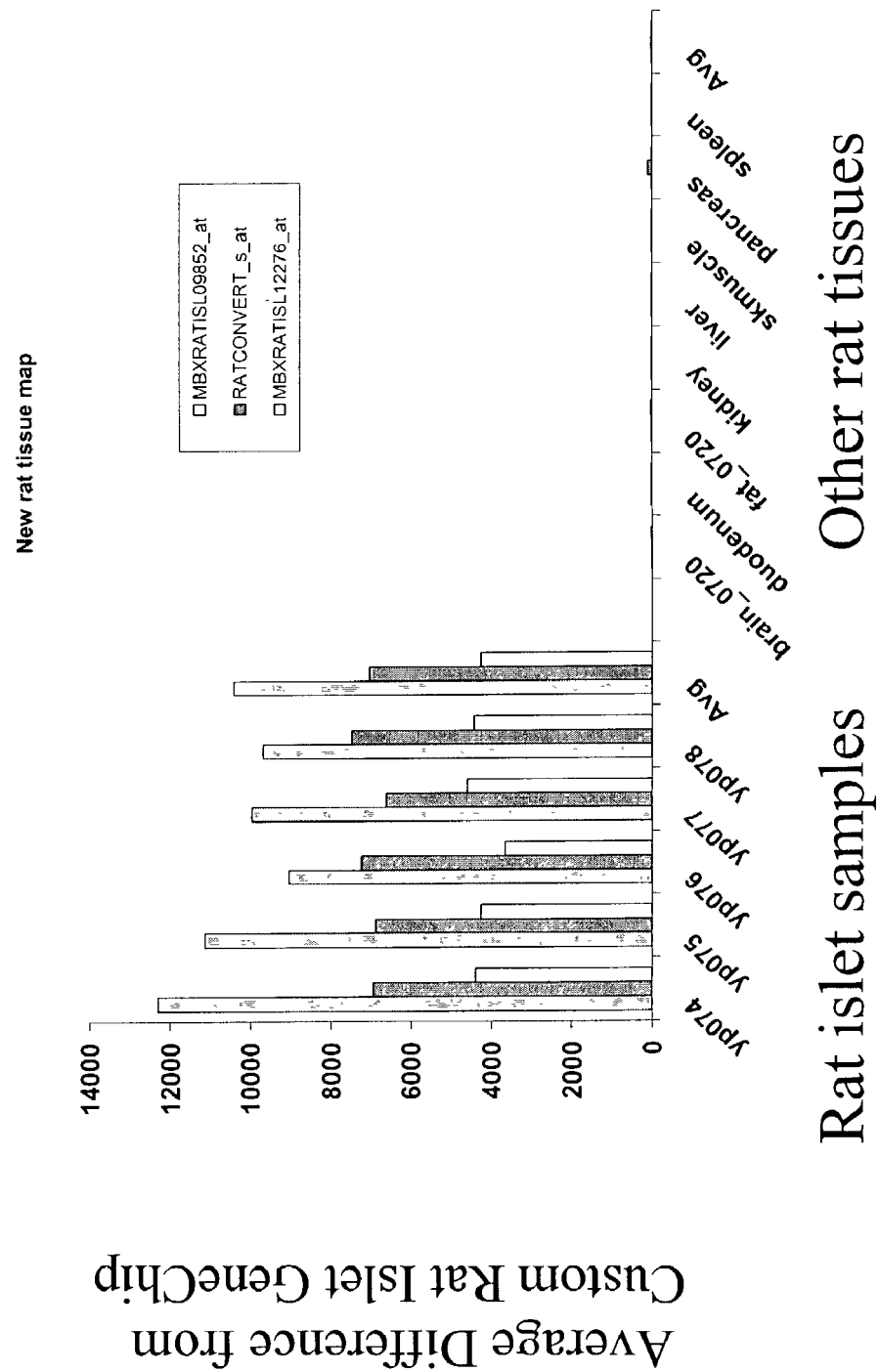
FIG. 1 illustrates the expression pattern of probe set MBXRATISL12276 in various tissues of rat.

This invention is directed to new polypeptide and polynucleotide sequences, designated Archipelin sequences, as well as methods of using the sequences to diagnose and treat diabetes. The present method also provides methods of identifying modulators of Archipelin expression and activity. Such modulators are useful for treating type 1 and type 2 diabetes as well as the pathological aspects of such diseases.

II. General Recombinant Nucleic Acids Methods for Use with the Invention

In numerous embodiments of the present invention, nucleic acids encoding a Archipelin of interest will be isolated and cloned using recombinant methods. Such embodiments are used, e.g., to isolate Archipelin polynucleotides (e.g., SEQ ID NO:1, SEQ ID NO:3, SEQ ID NO:5, and SEQ ID NO:8) for protein expression or during the generation of variants, derivatives, expression cassettes, or other sequences derived from an Archipelin polypeptide (e.g., SEQ ID NO:2, SEQ ID NO:4, SEQ ID NO:6, SEQ ID NO:7, and SEQ ID NOs:9–14), to monitor Archipelin gene expression, for the isolation or detection of Archipelin sequences in different species, for diagnostic purposes in a patient, e.g., to detect mutations in Archipelin or to detect expression levels of Archipelin nucleic acids or Archipelin polypeptides. In some embodiments, the sequences encoding the Archipelin of the invention are operably linked to a heterologous promoter. In one embodiment, the nucleic acids of the invention are from any mammal, including, in particular, e.g., a human, a mouse, a rat, etc.

A. General Recombinant Nucleic Acids Methods

This invention relies on routine techniques in the field of recombinant genetics. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized according to the solid phase phosphoramidite triester method first described by Beaucage & Caruthers, *Tetrahedron Letts.* 22:1859–1862 (1981), using an automated synthesizer, as described in Van Devanter et. al., *Nucleic Acids Res.* 12:6159–6168 (1984). Purification of oligonucleotides is by either native acrylamide gel electrophoresis or by anion-exchange HPLC as described in Pearson & Reanier, *J. Chrom.* 255:137–149 (1983).

The sequence of the cloned genes and synthetic oligonucleotides can be verified after cloning using, e.g., the chain termination method for sequencing double-stranded templates of Wallace et al., *Gene* 16:21–26 (1981).

B. Cloning Methods for the Isolation of Nucleotide Sequences Encoding the Desired Proteins In general, the nucleic acids encoding the subject proteins are cloned from DNA sequence libraries that are made to encode copy DNA (cDNA) or genomic DNA. The particular sequences can be located by hybridizing with an oligonucleotide probe, the sequence of which can be derived from the sequences provided herein (e.g., SEQ ID NO:1, SEQ ID NO:3, SEQ ID NO:5, and SEQ ID NO:8), which provides a reference for PCR primers and defines suitable regions for isolating Archipelin-specific probes. Alternatively, where the sequence is cloned into an expression library, the expressed recombinant protein can be detected immunologically with antisera or purified antibodies made against the Archipelin of interest.

Methods for making and screening genomic and cDNA libraries are well known to those of skill in the art (see, e.g., Gubler and Hoffman *Gene* 25:263–269 (1983); Benton and Davis *Science,* 196:180–182 (1977); and Sambrook, supra). A islet cells are an example of suitable cells to isolate Archipelin RNA and cDNA.

Briefly, to make the cDNA library, one should choose a source that is rich in mRNA. The mRNA can then be made into cDNA, ligated into a recombinant vector, and transfected into a recombinant host for propagation, screening and cloning. For a genomic library, the DNA is extracted from a suitable tissue and either mechanically sheared or enzymatically digested to yield fragments of preferably about 5–100 kb. The fragments are then separated by gradient centrifugation from undesired sizes and are constructed in bacteriophage lambda vectors. These vectors and phage are packaged in vitro, and the recombinant phages are analyzed by plaque hybridization. Colony hybridization is carried out as generally described in Grunstein et al., *Proc. Natl. Acad. Sci. USA.,* 72:3961–3965 (1975).

An alternative method combines the use of synthetic oligonucleotide primers with polymerase extension on an mRNA or DNA template. Suitable primers can be designed from specific Archipelin sequences, e.g., the sequences described in SEQ ID NO:1, SEQ ID NO:3, SEQ ID NO:5, and SEQ ID NO:8. This polymerase chain reaction (PCR) method amplifies the nucleic acids encoding the protein of interest directly from mRNA, cDNA, genomic libraries or cDNA libraries. Restriction endonuclease sites can be incorporated into the primers. Polymerase chain reaction or other in vitro amplification methods may also be useful, for example, to clone nucleic acids encoding specific proteins and express said proteins, to synthesize nucleic acids that will be used as probes for detecting the presence of mRNA encoding an Archipelin polypeptide of the invention in physiological samples, for nucleic acid sequencing, or for other purposes (see, U.S. Pat. Nos. 4,683,195 and 4,683, 202). Genes amplified by a PCR reaction can be purified from agarose gels and cloned into an appropriate vector.

Appropriate primers and probes for identifying the genes encoding an Archipelin polypeptide of the invention from mammalian tissues can be derived from the sequences provided herein, in particular SEQ ID NO:1, SEQ ID NO:3, SEQ ID NO:5, and SEQ ID NO:8. For a general overview of PCR, see, Innis et al. PCR Protocols: *A Guide to Methods and Applications*, Academic Press, San Diego (1990).

Synthetic oligonucleotides can be used to construct genes. This is done using a series of overlapping oligonucleotides, usually 40–120 bp in length, representing both the sense and anti-sense strands of the gene. These DNA fragments are then annealed, ligated and cloned.

A gene encoding an Archipelin polypeptide of the invention can be cloned using intermediate vectors before transformation into mammalian cells for expression. These intermediate vectors are typically prokaryote vectors or shuttle vectors. The proteins can be expressed in either prokaryotes, using standard methods well known to those of skill in the art, or eukaryotes as described infra.

C. Expression in Prokaryotes and Eukaryotes

To obtain high level expression of a cloned gene, such as cDNAs encoding Archipelin, one typically subclones polynucleotides encoding Archipelin into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al. and Ausubel et al. Bacterial expression systems for expressing the Archipelin protein are available in, e.g., *E. coli, Bacillus* sp., and *Salmonella* (Palva et al., *Gene* 22:229–235 (1983); Mosbach et al., *Nature* 302:543–545 (1983). Kits for such expression systems are commercially available. Eukaryotic expression systems for mammalian cells, yeast, and insect cells are well known in the art and are also commercially available.

Selection of the promoter used to direct expression of a heterologous nucleic acid depends on the particular application. The promoter is preferably positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of Archipelin-encoding nucleic acid in host cells. A typical expression cassette thus contains a promoter operably linked to the nucleic acid sequence encoding Archipelin and signals required for efficient polyadenylation of the transcript, ribosome binding sites, and translation termination. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ. Epitope tags can also be added to recombinant proteins to provide convenient methods of isolation, e.g., c-myc.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A$^+$, pMTO10/A$^+$, pMAMneo-5, baculovirus pDSVE, and any other vector allowing expression of proteins under the direction of the CMV promoter, SV40 early promoter, SV40 later promoter, metallothionein promoter, murine mammary tumor virus promoter, Rous sarcoma virus promoter, polyhedrin promoter, or other promoters shown effective for expression in eukaryotic cells.

Expression of proteins from eukaryotic vectors can be also be regulated using inducible promoters. With inducible promoters, expression levels are tied to the concentration of inducing agents, such as tetracycline or ecdysone, by the incorporation of response elements for these agents into the promoter. Generally, high level expression is obtained from inducible promoters only in the presence of the inducing agent; basal expression levels are minimal. Inducible expression vectors are often chosen if expression of the protein of interest is detrimental to eukaryotic cells.

Some expression systems have markers that provide gene amplification such as thymidine kinase and dihydrofolate reductase. Alternatively, high yield expression systems not involving gene amplification are also suitable, such as using a baculovirus vector in insect cells, with an Archipelin-encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are preferably chosen such that they do not interfere with the replication of the DNA in eukaryotic cells, if necessary.

Standard transfection methods are used to produce bacterial, mammalian, yeast or insect cell lines that express large quantities of Archipelin protein, which are then purified using standard techniques (see, e.g., Colley et al., *J. Biol. Chem.* 264:17619–17622 (1989); *Guide to Protein Purification*, in *Methods in Enzymology*, vol. 182 (Deutscher, ed., 1990)). Transformation of eukaryotic and prokaryotic cells are performed according to standard techniques (see, e.g., Morrison, *J. Bact.* 132:349–351 (1977); Clark-Curtiss & Curtiss, *Methods in Enzymology* 101:347–362 (Wu et al., eds, 1983).

Any of the well-known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing Archipelin.

After the expression vector is introduced into the cells, the transfected cells are cultured under conditions favoring expression of Archipelin, which is recovered from the culture using standard techniques identified below.

III. Purification of Proteins of the Invention

Either naturally occurring or recombinant Archipelin can be purified for use in functional assays. Naturally occurring Archipelin can be purified, e.g., from mouse or human tissue such as islet cells or any other source of an Archipelin ortholog. Recombinant Archipelin can be purified from any suitable expression system.

The Archipelin may be purified to substantial purity by standard techniques, including selective precipitation with such substances as ammonium sulfate; column chromatography, immunopurification methods, and others (see, e.g., Scopes, *Protein Purification: Principles and Practice* (1982); U.S. Pat. No. 4,673,641; Ausubel et al., supra; and Sambrook et al., supra).

A number of procedures can be employed when recombinant Archipelin are being purified. For example, proteins having established molecular adhesion properties can be reversible fused to Archipelin. With the appropriate ligand, Archipelin can be selectively adsorbed to a purification column and then freed from the column in a relatively pure form. The fused protein is then removed by enzymatic activity. Finally Archipelin can be purified using immunoaffinity columns.

A. Purification of Proteins from Recombinant Bacteria

When recombinant proteins are expressed by the transformed bacteria in large amounts, typically after promoter induction, although expression can be constitutive, the proteins may form insoluble aggregates. There are several protocols that are suitable for purification of protein inclusion bodies. For example, purification of aggregate proteins (hereinafter referred to as inclusion bodies) typically involves the extraction, separation and/or purification of inclusion bodies by disruption of bacterial cells typically, but not limited to, by incubation in a buffer of about 100–150 μg/ml lysozyme and 0.1% Nonidet P40, a non-ionic detergent. The cell suspension can be ground using a Polytron grinder (Brinkman Instruments, Westbury, N.Y.). Alternatively, the cells can be sonicated on ice. Alternate methods of lysing bacteria are described in Ausubel et al. and Sambrook et al., both supra, and will be apparent to those of skill in the art.

The cell suspension is generally centrifuged and the pellet containing the inclusion bodies resuspended in buffer which does not dissolve but washes the inclusion bodies, e.g., 20 mM Tris-HCl (pH 7.2), 1 mM EDTA, 150 mM NaCl and 2% Triton-X 100, a non-ionic detergent. It may be necessary to repeat the wash step to remove as much cellular debris as possible. The remaining pellet of inclusion bodies may be resuspended in an appropriate buffer (e.g., 20 mM sodium phosphate, pH 6.8, 150 mM NaCl). Other appropriate buffers will be apparent to those of skill in the art.

Following the washing step, the inclusion bodies are solubilized by the addition of a solvent that is both a strong hydrogen acceptor and a strong hydrogen donor (or a combination of solvents each having one of these properties). The proteins that formed the inclusion bodies may then be renatured by dilution or dialysis with a compatible buffer. Suitable solvents include, but are not limited to, urea (from about 4 M to about 8 M), formamide (at least about 80%, volume/volume basis), and guanidine hydrochloride (from about 4 M to about 8 M). Some solvents that are capable of solubilizing aggregate-forming proteins, such as SDS (sodium dodecyl sulfate) and 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of the immunologically and/or biologically active protein of interest. After solubilization, the protein can be separated from other bacterial proteins by standard separation techniques.

Alternatively, it is possible to purify proteins from bacteria periplasm. Where the protein is exported into the periplasm of the bacteria, the periplasmic fraction of the bacteria can be isolated by cold osmotic shock in addition to other methods known to those of skill in the art (see, Ausubel et al., supra). To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

B. Purification of Proteins from Insect Cells

Proteins can also be purified from eukaryotic gene expression systems as described in, e.g., Fernandez and Hoeffler, *Gene Expression Systems* (1999). In some embodiments, baculovirus expression systems are used to isolate Archipelin proteins or other proteins of the invention. Recombinant cabulaoviruses are generally generated by replacing the polyhedrin coding sequence of a baculovirus with a gene to be expressed (e.g., an Archipelin polynucleotide). Viruses lacking the polyhedrin gene have a unique plaque morphology making them easy to recognize. In some embodiments, a recombinant baculovirus is generated by first cloning a polynucleotide of interest into a transfer vector (e.g., a pUC based vector) such that the polynucleotide is operably linked to a polyhedrin promoter. The transfer vector is transfected with wildtype DNA into an insect cell (e.g., Sf9, Sf21 or BT1-TN-5B1-4 cells), resulting in homologous recombination and replacement of the polyhedrin gene in the wildtype viral DNA with the polynucleotide of interest. Virus can then be generated and plaque purified. Protein expression results upon viral infection of insect cells. Expressed proteins can be harvested from cell supernatant if secreted, or from cell lysates if intracellular. See, e.g., Ausubel et al. and Fernandez and Hoeffler, supra.

C. Standard Protein Separation Techniques for Purifying Proteins

1. Solubility Fractionation

Often as an initial step, and if the protein mixture is complex, an initial salt fractionation can separate many of the unwanted host cell proteins (or proteins derived from the cell culture media) from the recombinant protein of interest. The salt used for fractionation can be, e.g., ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol is to add saturated ammonium sulfate to a protein solution so that the resultant ammonium sulfate concentration is between 20–30%. This will precipitate the most hydrophobic proteins. The precipitate is discarded (unless the protein of interest is hydrophobic) and ammonium sulfate is added to the supernatant to a concentration known to precipitate the protein of interest. The precipitate is then solubilized in buffer and the excess salt removed if necessary, through either dialysis or diafiltration. Other methods that rely on solubility of proteins, such as cold ethanol precipitation, are well known to those of skill in the art and can be used to fractionate complex protein mixtures.

2. Size Differential Filtration

Based on a calculated molecular weight, a protein of greater and lesser size can be isolated using ultrafiltration through membranes of different pore sizes (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

3. Column Chromatography

The proteins of interest can also be separated from other proteins on the basis of their size, net surface charge, hydrophobicity and affinity for ligands. In addition, antibodies raised against proteins can be conjugated to column matrices and the proteins immunopurified. All of these methods are well known in the art.

It will be apparent to one of skill that chromatographic techniques can be performed at any scale and using equipment from many different manufacturers (e.g., Pharmacia Biotech).

IV. Detection of Gene Expression

Those of skill in the art will recognize that detection of expression of Archipelin polynucleotides has many uses. For example, as discussed herein, detection of Archipelin levels in a patient is useful for diagnosing diabetes or a predisposition for at least some of the pathological effects of diabetes.

A variety of methods of specific DNA and RNA measurement using nucleic acid hybridization techniques are known to those of skill in the art (see, Sambrook, supra). Some methods involve an electrophoretic separation (e.g., Southern blot for detecting DNA, and Northern blot for detecting RNA), but measurement of DNA and RNA can also be carried out in the absence of electrophoretic separation (e.g., by dot blot). Southern blot of genomic DNA (e.g., from a human) can be used for screening for restriction fragment length polymorphism (RFLP) to detect the presence of a genetic disorder affecting an Archipelin polypeptide of the invention.

The selection of a nucleic acid hybridization format is not critical. A variety of nucleic acid hybridization formats are known to those skilled in the art. For example, common formats include sandwich assays and competition or displacement assays. Hybridization techniques are generally described in Hames and Higgins *Nucleic Acid Hybridization, A Practical Approach*, IRL Press (1985); Gall and Pardue, *Proc. Natl. Acad. Sci. U.S.A.*, 63:378–383 (1969); and John et al. *Nature*, 223:582–587 (1969).

Detection of a hybridization complex may require the binding of a signal generating complex to a duplex of target and probe polynucleotides or nucleic acids. Typically, such binding occurs through ligand and anti-ligand interactions as between a ligand-conjugated probe and an anti-ligand conjugated with a signal. The binding of the signal generation complex is also readily amenable to accelerations by exposure to ultrasonic energy.

The label may also allow indirect detection of the hybridization complex. For example, where the label is a hapten or antigen, the sample can be detected by using antibodies. In these systems, a signal is generated by attaching fluorescent or enzyme molecules to the antibodies or in some cases, by attachment to a radioactive label (see, e.g., Tijssen, "*Practice and Theory of Enzyme Immunoassays,*" *Laboratory Techniques in Biochemistry and Molecular Biology*, Burdon and van Knippenberg Eds., Elsevier (1985), pp. 9–20).

The probes are typically labeled either directly, as with isotopes, chromophores, lumiphores, chromogens, or indirectly, such as with biotin, to which a streptavidin complex may later bind. Thus, the detectable labels used in the assays of the present invention can be primary labels (where the label comprises an element that is detected directly or that produces a directly detectable element) or secondary labels (where the detected label binds to a primary label, e.g., as is common in immunological labeling). Typically, labeled signal nucleic acids are used to detect hybridization. Complementary nucleic acids or signal nucleic acids may be labeled by any one of several methods typically used to detect the presence of hybridized polynucleotides. The most common method of detection is the use of autoradiography with $^3$H, $^{125}$I, $^{35}$S, $^{14}$C, or $^{32}$P-labeled probes or the like.

Other labels include, e.g., ligands which bind to labeled antibodies, fluorophores, chemiluminescent agents, enzymes, and antibodies which can serve as specific binding pair members for a labeled ligand. An introduction to labels, labeling procedures and detection of labels is found in Polak and Van Noorden *Introduction to Immunocytochemistry*, 2nd ed., Springer Verlag, N.Y. (1997); and in Haugland *Handbook of Fluorescent Probes and Research Chemicals*, a combined handbook and catalogue Published by Molecular Probes, Inc. (1996).

In general, a detector which monitors a particular probe or probe combination is used to detect the detection reagent label. Typical detectors include spectrophotometers, phototubes and photodiodes, microscopes, scintillation counters, cameras, film and the like, as well as combinations thereof. Examples of suitable detectors are widely available from a variety of commercial sources known to persons of skill in the art. Commonly, an optical image of a substrate comprising bound labeling moieties is digitized for subsequent computer analysis.

Most typically, the amount of, for example, an Archipelin RNA is measured by quantitating the amount of label fixed to the solid support by binding of the detection reagent. Typically, the presence of a modulator during incubation will increase or decrease the amount of label fixed to the solid support relative to a control incubation which does not comprise the modulator, or as compared to a baseline established for a particular reaction type. Means of detecting and quantitating labels are well known to those of skill in the art.

In some embodiments, the target nucleic acid or the probe is immobilized on a solid support. Solid supports suitable for use in the assays of the invention are known to those of skill in the art. As used herein, a solid support is a matrix of material in a substantially fixed arrangement.

A variety of automated solid-phase assay techniques are also appropriate. For instance, very large scale immobilized polymer arrays (VLSIPS™), available from Affymetrix, Inc. in Santa Clara, Calif. can be used to detect changes in expression levels of a plurality of genes involved in the same regulatory pathways simultaneously. See, Tijssen, supra., Fodor et al. (1991) *Science*, 251: 767–777; Sheldon et al.

(1993) *Clinical Chemistry* 39(4): 718–719, and Kozal et al. (1996) *Nature Medicine* 2(7): 753–759.

Detection can be accomplished, for example, by using a labeled detection moiety that binds specifically to duplex nucleic acids (e.g., an antibody that is specific for RNA-DNA duplexes). One example uses an antibody that recognizes DNA-RNA heteroduplexes in which the antibody is linked to an enzyme (typically by recombinant or covalent chemical bonding). The antibody is detected when the enzyme reacts with its substrate, producing a detectable product. Coutlee et al. (1989) *Analytical Biochemistry* 181: 153–162; Bogulavski (1986) et al. *J. Immunol. Methods* 89:123–130; Prooijen-Knegt (1982) *Exp. Cell Res.* 141: 397–407; Rudkin (1976) *Nature* 265:472–473, Stollar (1970) *PNAS* 65:993–1000; Ballard (1982) *Mol. Immunol.* 19:793–799; Pisetsky and Caster (1982) *Mol. Immunol.* 19:645–650; Viscidi et al. (1988) *J. Clin. Microbial.* 41:199–209; and Kiney et al. (1989) *J. Clin. Microbiol.* 27:6–12 describe antibodies to RNA duplexes, including homo and heteroduplexes. Kits comprising antibodies specific for DNA:RNA hybrids are available, e.g., from Digene Diagnostics, Inc. (Beltsville, Md.).

In addition to available antibodies, one of skill in the art can easily make antibodies specific for nucleic acid duplexes using existing techniques, or modify those antibodies which are commercially or publicly available. In addition to the art referenced above, general methods for producing polyclonal and monoclonal antibodies are known to those of skill in the art (see, e.g., Paul (ed) *Fundamental Immunology, Third Edition* Raven Press, Ltd., NY (1993); Coligan *Current Protocols in Immunology* Wiley/Greene, N.Y. (1991); Harlow and Lane *Antibodies. A Laboratory Manual* Cold Spring Harbor Press, NY (1989); Stites et al. (eds.) *Basic and Clinical Immunology* (4th ed.) Lange Medical Publications, Los Altos, Calif., and references cited therein; Goding *Monoclonal Antibodies: Principles and Practice* (2d ed.) Academic Press, New York, N.Y., (1986); and Kohler and Milstein *Nature* 256: 495–497 (1975)). Other suitable techniques for antibody preparation include selection of libraries of recombinant antibodies in phage or similar vectors (see, Huse et al. *Science* 246:1275–1281 (1989); and Ward et al. *Nature* 341:544–546 (1989)). Specific monoclonal and polyclonal antibodies and antisera will usually bind with a $K_D$ of at least about 0.1 µM, preferably at least about 0.01 µM or better, and most typically and preferably, 0.001 µM or better.

The nucleic acids used in this invention can be either positive or negative probes. Positive probes bind to their targets and the presence of duplex formation is evidence of the presence of the target. Negative probes fail to bind to the suspect target and the absence of duplex formation is evidence of the presence of the target. For example, the use of a wild type specific nucleic acid probe or PCR primers may serve as a negative probe in an assay sample where only the nucleotide sequence of interest is present.

The sensitivity of the hybridization assays maybe enhanced through use of a nucleic acid amplification system that multiplies the target nucleic acid being detected. Examples of such systems include the polymerase chain reaction (PCR) system and the ligase chain reaction (LCR) system. Other methods described in the art are the nucleic acid sequence based amplification (NASBA, Cangene, Mississauga, Ontario) and Q Beta Replicase systems. These systems can be used to directly identify mutants where the PCR or LCR primers are designed to be extended or ligated only when a selected sequence is present. Alternatively, the selected sequences can be generally amplified using, for example, nonspecific PCR primers and the amplified target region later probed for a specific sequence indicative of a mutation.

An alternative means for determining the level of expression of the nucleic acids of the present invention is in situ hybridization. In situ hybridization assays are well known and are generally described in Angerer et al, *Methods Enzymol.* 152:649–660 (1987). In an in situ hybridization assay, cells, preferentially human pancreatic cells such as islet cells, are fixed to a solid support, typically a glass slide. If DNA is to be probed, the cells are denatured with heat or alkali. The cells are then contacted with a hybridization solution at a moderate temperature to permit annealing of specific probes that are labeled. The probes are preferably labeled with radioisotopes or fluorescent reporters.

V. Immunological Detection of Archipelin

In addition to the detection of Archipelin genes and gene expression using nucleic acid hybridization technology, one can also use immunoassays to detect Archipelin polypeptides. Immunoassays can be used to qualitatively or quantitatively analyze Archipelin. A general overview of the applicable technology can be found in Harlow & Lane, *Antibodies: A Laboratory Manual* (1988).

A. Antibodies to Target Proteins

Methods for producing polyclonal and monoclonal antibodies that react specifically with a protein of interest are known to those of skill in the art (see, e.g., Coligan, supra; and Harlow and Lane, supra; Stites et al., supra and references cited therein; Goding, supra; and Kohler and Milstein *Nature*, 256:495–497 (1975)). Such techniques include antibody preparation by selection of antibodies from libraries of recombinant antibodies in phage or similar vectors (see, Huse et al., supra; and Ward et al., supra). For example, in order to produce antisera for use in an immunoassay, the protein of interest or an antigenic fragment thereof, is isolated as described herein. For example, a recombinant protein is produced in a transformed cell line. An inbred strain of mice or rabbits is immunized with the protein using a standard adjuvant, such as Freund's adjuvant, and a standard immunization protocol. Alternatively, a synthetic peptide derived from the sequences disclosed herein and conjugated to a carrier protein can be used as an immunogen.

Polyclonal sera are collected and titered against the immunogen protein in an immunoassay, for example, a solid phase immunoassay with the immunogen immobilized on a solid support. Polyclonal antisera with a titer of $10^4$ or greater are selected and tested for their crossreactivity against non-Archipelin proteins or even other homologous proteins from other organisms, using a competitive binding immunoassay. Specific monoclonal and polyclonal antibodies and antisera will usually bind with a $K_D$ of at least about 0.1 mM, more usually at least about 1 µM, preferably at least about 0.1 µM or better, and most preferably, 0.01 µM or better.

For preparation of antibodies, e.g., recombinant, monoclonal, or polyclonal antibodies, many technique known in the art can be used (see, e.g., Kohler & Milstein, *Nature* 256:495–497 (1975); Kozbor et al., *Immunology Today* 4: 72 (1983); Cole et al., pp. 77–96 in *Monoclonal Antibodies and Cancer Therapy*, Alan R. Liss, Inc. (1985); Coligan, *Current Protocols in Immunology* (1991); Harlow & Lane, *Antibodies, A Laboratory Manual* (1988); and Goding, *Monoclonal Antibodies: Principles and Practice* (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, *Immunology* (3rd ed. 1997)). Techniques for the production of single chain antibodies or recombinant antibodies (U.S. Pat. No. 4,946,778, U.S. Pat. No. 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625, 126; 5,633,425; 5,661,016, Marks et al., *Bio/Technology* 10:779–783 (1992); Lonberg et al., *Nature* 368:856–859 (1994); Morrison, *Nature* 368:812–13 (1994); Fishwild et al., *Nature Biotechnology* 14:845–51 (1996); Neuberger, *Nature Biotechnology* 14:826 (1996); and Lonberg & Huszar, *Intern. Rev. Immunol.* 13:65–93 (1995)). Alternatively, phage display technology can be used to identify antibodies and heteromeric Fab fragments that specifically bind to selected antigens (see, e.g., McCafferty et al., *Nature* 348:552–554 (1990); Marks et al, *Biotechnology* 10:779–783 (1992)). Antibodies can also be made bispecific, i.e., able to recognize two different antigens (see, e.g., WO 93/08829, Traunecker et al., *EMBO J.* 10:3655–3659 (1991); and Suresh et al., *Methods in Enzymology* 121:210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

Methods for humanizing or primatizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Jones et al., *Nature* 321:522–525 (1986); Riechmann et al., *Nature* 332: 323–327 (1988); Verhoeyen et al., *Science* 239:1534–1536 (1988) and Presta, *Curr. Op. Struct. Biol.* 2:593–596 (1992)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

A number of proteins of the invention comprising immunogens may be used to produce antibodies specifically or selectively reactive with the proteins of interest. Recombinant protein is an exemplary immunogen for the production of monoclonal or polyclonal antibodies. Naturally occurring protein may also be used either in pure or impure form. Synthetic peptides made using the protein sequences described herein may also be used as an immunogen for the production of antibodies to the protein. Recombinant protein can be expressed in eukaryotic or prokaryotic cells and purified as generally described supra. The product is then injected into an animal capable of producing antibodies. Either monoclonal or polyclonal antibodies may be generated for subsequent use in immunoassays to measure the protein.

Methods of production of polyclonal antibodies are known to those of skill in the art. In brief, an immunogen, preferably a purified protein, is mixed with an adjuvant and animals are immunized. The animal's immune response to the immunogen preparation is monitored by taking test bleeds and determining the titer of reactivity to the Archipelin of interest. When appropriately high titers of antibody to the immunogen are obtained, blood is collected from the animal and antisera are prepared. Further fractionation of the antisera to enrich for antibodies reactive to the protein can be done if desired (see, Harlow and Lane, supra).

Monoclonal antibodies may be obtained using various techniques familiar to those of skill in the art. Typically, spleen cells from an animal immunized with a desired antigen are immortalized, commonly by fusion with a myeloma cell (see, Kohler and Milstein, *Eur. J. Immunol.* 6:511–519 (1976)). Alternative methods of immortalization include, e.g., transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse et al., supra.

Once target protein specific antibodies are available, the protein can be measured by a variety of immunoassay methods with qualitative and quantitative results available to the clinician. For a review of immunological and immunoassay procedures in general see, Stites, supra. Moreover, the immunoassays of the present invention can be performed in any of several configurations, which are reviewed extensively in Maggio *Enzyme Immunoassay*, CRC Press, Boca Raton, Fla. (1980); Tijssen, supra; and Harlow and Lane, supra.

Immunoassays to measure target proteins in a human sample may use a polyclonal antiserum which was raised to the protein (e.g., SEQ ID NO:2, SEQ ID NO:7 and SEQ ID NOs:9–14) at least partially encoded by a sequence described herein (e.g., SEQ ID NO:1 and SEQ ID NO:8) or a fragment thereof. This antiserum is selected to have low cross-reactivity against non-Archipelin proteins and any such cross-reactivity is removed by immunoabsorption prior to use in the immunoassay.

Polyclonal antibodies that specifically bind to an Archipelin of interest from a particular species can be made by subtracting out cross-reactive antibodies using Archipelin homologs. In an analogous fashion, antibodies specific to a particular Archipelin (e.g., the human Archipelin polypeptide) can be obtained in an organism with multiple Archipelin genes by subtracting out cross-reactive antibodies using other Archipelin.

B. Immunological Binding Assays

In some embodiments, a protein of interest is detected and/or quantified using any of a number of well known immunological binding assays (see, e.g., U.S. Pat. Nos. 4,366,241; 4,376,110; 4,517,288; and 4,837,168). For a review of the general immunoassays, see also Asai *Methods in Cell Biology Volume 37: Antibodies in Cell Biology*, Academic Press, Inc. NY (1993); Stites, supra. Immunological binding assays (or immunoassays) typically utilize a "capture agent" to specifically bind to and often immobilize the analyte (in this case an Archipelin of the present invention or antigenic subsequences thereof). The capture agent is a moiety that specifically binds to the analyte. In some embodiments, the capture agent is an antibody that specifically binds, for example, an Archipelin polypeptide of the invention. The antibody (e.g., anti-Archipelin antibody) may be produced by any of a number of means well known to those of skill in the art and as described above.

Immunoassays also often utilize a labeling agent to specifically bind to and label the binding complex formed by the capture agent and the analyte. The labeling agent may itself be one of the moieties comprising the antibody/analyte complex. Thus, the labeling agent may be a labeled Archipelin polypeptide or a labeled anti-Archipelin receptor antibody. Alternatively, the labeling agent may be a third moiety, such as another antibody, that specifically binds to the antibody/protein complex.

In some embodiments, the labeling agent is a second antibody bearing a label. Alternatively, the second antibody may lack a label, but it may, in turn, be bound by a labeled third antibody specific to antibodies of the species from which the second antibody is derived. The second antibody can be modified with a detectable moiety, such as biotin, to which a third labeled molecule can specifically bind, such as enzyme-labeled streptavidin.

Other proteins capable of specifically binding immunoglobulin constant regions, such as protein A or protein G, can also be used as the label agents. These proteins are normal constituents of the cell walls of streptococcal bacteria. They exhibit a strong non-immunogenic reactivity with immunoglobulin constant regions from a variety of species (see, generally, Kronval, et al. *J. Immunol.*, 111:1401–1406 (1973); and Akerstrom, et al. *J. Immunol.*, 135:2589–2542 (1985)).

Throughout the assays, incubation and/or washing steps may be required after each combination of reagents. Incubation steps can vary from about 5 seconds to several hours, preferably from about 5 minutes to about 24 hours. The incubation time will depend upon the assay format, analyte, volume of solution, concentrations, and the like. Usually, the assays will be carried out at ambient temperature, although they can be conducted over a range of temperatures, such as 10° C. to 40° C.

1. Non-Competitive Assay Formats

Immunoassays for detecting proteins of interest from tissue samples may be either competitive or noncompetitive. Noncompetitive immunoassays are assays in which the amount of captured analyte (in this case the protein) is directly measured. In one "sandwich" assay, for example, the capture agent (e.g., anti-Archipelin antibodies) can be bound directly to a solid substrate where it is immobilized. These immobilized antibodies then capture the Archipelin present in the test sample. The Archipelin thus immobilized is then bound by a labeling agent, such as a second anti-Archipelin receptor antibody bearing a label. Alternatively, the second antibody may lack a label, but it may, in turn, be bound by a labeled third antibody specific to antibodies of the species from which the second antibody is derived. The second can be modified with a detectable moiety, such as biotin, to which a third labeled molecule can specifically bind, such as enzyme-labeled streptavidin.

2. Competitive Assay Formats

In competitive assays, the amount of target protein (analyte) present in the sample is measured indirectly by measuring the amount of an added (exogenous) analyte (i.e., the Archipelin of interest) displaced (or competed away) from a capture agent (i.e., anti antibody) by the analyte present in the sample. In one competitive assay, a known amount of, in this case, the protein of interest is added to the sample and the sample is then contacted with a capture agent, in this case an antibody that specifically binds to the Archipelin of interest. The amount of Archipelin bound to the antibody is inversely proportional to the concentration of Archipelin present in the sample. In some embodiments, the antibody is immobilized on a solid substrate. The amount of the Archipelin bound to the antibody may be determined either by measuring the amount of subject protein present in a Archipelin protein/antibody complex or, alternatively, by measuring the amount of remaining uncomplexed protein. The amount of Archipelin protein may be detected by providing a labeled Archipelin protein molecule.

A hapten inhibition assay is another exemplary competitive assay. In this assay, a known analyte, in this case the target protein, is immobilized on a solid substrate. A known amount of anti-Archipelin antibody is added to the sample, and the sample is then contacted with the immobilized target. In this case, the amount of anti-Archipelin antibody bound to the immobilized Archipelin is inversely proportional to the amount of Archipelin protein present in the sample. Again, the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

Immunoassays in the competitive binding format can be used for cross-reactivity determinations. For example, the protein encoded by the sequences described herein can be immobilized on a solid support. Proteins are added to the assay which compete with the binding of the antisera to the immobilized antigen. The ability of the above proteins to compete with the binding of the antisera to the immobilized protein is compared to that of the protein encoded by any of the sequences described herein. The percent cross-reactivity for the above proteins is calculated, using standard calculations. Those antisera with less than 10% cross-reactivity with each of the proteins listed above are selected and pooled. The cross-reacting antibodies are optionally removed from the pooled antisera by immunoabsorption with the considered proteins, e.g., distantly related homologs.

The immunoabsorbed and pooled antisera are then used in a competitive binding immunoassay as described above to compare a second protein, thought to be perhaps a protein of the present invention, to the immunogen protein. In order to make this comparison, the two proteins are each assayed at a wide range of concentrations and the amount of each protein required to inhibit 50% of the binding of the antisera to the immobilized protein is determined. If the amount of the second protein required is less than times the amount of the protein partially encoded by a sequence herein that is required, then the second protein is said to specifically bind to an antibody generated to an immunogen consisting of the target protein.

3. Other Assay Formats

In some embodiments, western blot (immunoblot) analysis is used to detect and quantify the presence of an Archipelin of the invention in the sample. The technique generally comprises separating sample proteins by gel electrophoresis on the basis of molecular weight, transferring the separated proteins to a suitable solid support (such as, e.g., a nitrocellulose filter, a nylon filter, or a derivatized nylon filter) and incubating the sample with the antibodies that specifically bind the protein of interest. For example, the anti-Archipelin antibodies specifically bind to the Archipelin on the solid support. These antibodies may be directly labeled or alternatively may be subsequently detected using labeled antibodies (e.g., labeled sheep anti-mouse antibodies) that specifically bind to the antibodies against the protein of interest.

Other assay formats include liposome immunoassays (LIA), which use liposomes designed to bind specific molecules (e.g., antibodies) and release encapsulated reagents or markers. The released chemicals are then detected according to standard techniques (see, Monroe et al. (1986) *Amer. Clin. Prod. Rev.* 5:34–41).

4. Labels

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most labels useful in such methods can be applied to the present invention. Thus, a label is any composition detectable by spectroscopic, photochemical, biochemical, immunochemical, electrical, optical or chemical means. Useful labels in the present invention include magnetic beads (e.g., Dynabeads™), fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic (e.g., polystyrene, polypropylene, latex, etc.) beads.

The label may be coupled directly or indirectly to the desired component of the assay according to methods well known in the art. As indicated above, a wide variety of labels may be used, with the choice of label depending on the sensitivity required, the ease of conjugation with the compound, stability requirements, available instrumentation, and disposal provisions.

Non-radioactive labels are often attached by indirect means. The molecules can also be conjugated directly to signal generating compounds, e.g., by conjugation with an enzyme or fluorescent compound. A variety of enzymes and fluorescent compounds can be used with the methods of the present invention and are well-known to those of skill in the art (for a review of various labeling or signal producing systems which may be used, see, e.g., U.S. Pat. No. 4,391, 904).

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple colorimetric labels may be detected directly by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need to be labeled and the presence of the target antibody is detected by simple visual inspection.

VI. Screening for Modulators of Archipelin

Modulators of Archipelin, i.e. agonists or antagonists or agents of Archipelin activity or modulators of Archipelin polypeptide or polynucleotide expression, are useful for treating a number of human diseases, including diabetes. Administration of Archipelin agonists or agents that increase expression of Archipelin can be used to treat diabetic patients. For example, insufficient Archipelin due to functional impairment of islets may contribute to some of the pathologies associated with diabetes. Thus, restoration of Archipelin ameliorates some of these pathologies.

Conversely, under conditions of islet hyperactivity, such as occurs in an insulin resistant states, islet expansion may lead to overproduction of Archipelin. Overproduction leads to a different set of deleterious physiological effects that can be relieved by Archipelin antagonists. Archipelin agonists or antagonists may have beneficial physiological effects in diabetes whether or not the endogenous level of the peptide is abnormal.

A. Methods for identifying Modulators of Archipelin

A number of different screening protocols can be utilized to identify agents that modulate the level of expression or activity of Archipelin in cells, particularly mammalian cells, and especially human cells. In general terms, the screening methods involve screening a plurality of agents to identify an agent that modulates the activity of Archipelin by binding to Archipelin, preventing an inhibitor from binding to Archipelin or activating expression of Archipelin, for example.

1. Archipelin Binding Assays

Preliminary screens can be conducted by screening for compounds capable of binding to Archipelin, as at least some of the compounds so identified are likely Archipelin activators. The binding assays usually involve contacting an Archipelin protein with one or more test compounds and allowing sufficient time for the protein and test compounds to form a binding complex. Any binding complexes formed can be detected using any of a number of established analytical techniques. Protein binding assays include, but are not limited to, methods that measure co-precipitation, co-migration on non-denaturing SDS-polyacrylamide gels, and co-migration on Western blots (see, e.g., Bennet, J. P. and Yamamura, H. I. (1985) "Neurotransmitter, Hormone or Drug Receptor Binding Methods," in *Neurotransmitter Receptor Binding* (Yamamura, H. I., et al., eds.), pp. 61–89) as well as phage display and other binding assays known to those of skill in the art. The Archipelin protein utilized in such assays can be naturally expressed, cloned or synthesized Archipelin. In some embodiments, two hybrid assays, or other expression-based in vivo binding assays can be used. See, e.g., Fields, et al., *Nature* 340(6230):245–6 (1989).

Binding assays are also useful, e.g., for identifying endogenous proteins that interact with Archipelin. For example, receptors that bind Archipelin can be identified in binding assays.

2. Expression Assays

Certain screening methods involve screening for a compound that up-regulates the expression of Archipelin. Such methods generally involve conducting cell-based assays in which test compounds are contacted with one or more cells expressing Archipelin and then detecting an increase or decrease in Archipelin expression (either transcript or translation product). Some assays are performed with pancreatic islet cells, or other cells, that express endogenous Archipelin.

Archipelin expression can be detected in a number of different ways. As described herein, the expression level of Archipelin in a cell can be determined by probing the mRNA expressed in a cell with a probe that specifically hybridizes with a transcript (or complementary nucleic acid derived therefrom) of Archipelin. Probing can be conducted by lysing the cells and conducting Northern blots or without lysing the cells using in situ-hybridization techniques (see above). Alternatively, Archipelin protein can be detected using immunological methods in which a cell lysate is probe with antibodies that specifically bind to Archipelin.

Other cell-based assays are reporter assays conducted with cells that do not express Archipelin. Certain of these assays are conducted with a heterologous nucleic acid construct that includes a Archipelin promoter that is operably linked to a reporter gene that encodes a detectable product. A number of different reporter genes can be utilized. Some reporters are inherently detectable. An example of such a reporter is green fluorescent protein that emits fluorescence that can be detected with a fluorescence detector. Other reporters generate a detectable product. Often such reporters are enzymes. Exemplary enzyme reporters include, but are not limited to, β-glucuronidase, CAT (chloramphenicol acetyl transferase; Alton and Vapnek (1979) *Nature* 282:864–869), luciferase, β-galactosidase and alkaline phosphatase (Toh, et al. (1980) *Eur. J. Biochem.* 182:231–238; and Hall et al. (1983) *J. Mol. Appl. Gen.* 2:101).

In these assays, cells harboring the reporter construct are contacted with a test compound. A test compound that either modulates the activity of the promoter by binding to it or triggers a cascade that produces a molecule that modulates the promoter causes expression of the detectable reporter. Certain other reporter assays are conducted with cells that harbor a heterologous construct that includes a transcriptional control element that activates expression of Archipelin and a reporter operably linked thereto. Here, too, an agent that binds to the transcriptional control element to activate expression of the reporter or that triggers the formation of an agent that binds to the transcriptional control element to activate reporter expression, can be identified by the generation of signal associated with reporter expression.

The level of expression or activity can be compared to a baseline value. As indicated above, the baseline value can be a value for a control sample or a statistical value that is representative of Archipelin expression levels for a control population (e.g., healthy individuals not having or at risk for type 1 or type 2 diabetes). Expression levels can also be determined for cells that do not express Archipelin as a negative control. Such cells generally are otherwise substantially genetically the same as the test cells.

A variety of different types of cells can be utilized in the reporter assays. As stated above, certain cells are nerve cells that express an endogenous Archipelin. Cells not expressing Archipelin can be prokaryotic, but preferably are eukaryotic. The eukaryotic cells can be any of the cells typically utilized in generating cells that harbor recombinant nucleic acid constructs. Exemplary eukaryotic cells include, but are not limited to, yeast, and various higher eukaryotic cells such as the COS, CHO and HeLa cell lines.

Various controls can be conducted to ensure that an observed activity is authentic including running parallel reactions with cells that lack the reporter construct or by not contacting a cell harboring the reporter construct with test compound. Compounds can also be further validated as described below.

3. Validation

Compounds that are initially identified by any of the foregoing screening methods can be further tested to validate the apparent activity. Preferably such studies are conducted with suitable animal models. The basic format of such methods involves administering a lead compound identified during an initial screen to an animal that serves as a model for humans and then determining if Archipelin is in fact modulated. The animal models utilized in validation studies generally are mammals of any kind. Specific examples of suitable animals include, but are not limited to, primates, mice and rats.

B. Modulators of Archipelin

The compounds tested as modulators of Archipelin can be any small chemical compound, or a biological entity, such as a protein, sugar, nucleic acid or lipid. Alternatively, modulators can be genetically altered versions of an Archipelin gene or gene product. Typically, test compounds will be small chemical molecules and peptides. Essentially any chemical compound can be used as a potential modulator or ligand in the assays of the invention, although most often compounds that can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs, Switzerland) and the like.

In some embodiments, high throughput screening methods involve providing a combinatorial chemical or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487–493 (1991) and Houghton et al., *Nature* 354:84–88 (1991)). Other chemistries for generating chemical diversity libraries can also be used. Such chemistries include, but are not limited to: peptoids (e.g., PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909–6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217–9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology*, 14(3):309–314 (1996) and PCT/US96/10287), carbohydrate libraries (see, e.g., Liang et al., *Science*, 274: 1520–1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Tripos, Inc., St. Louis, Mo., 3D Pharmaceuticals, Exton, Pa., Martek Biosciences, Columbia, Md., etc.).

C. Solid Phase and Soluble High Throughput Assays

In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5–10 wells can test a single modulator. Thus, a single standard microtiter plate can assay about 100 (e.g., 96) modulators. If 1536 well plates are used, then a single plate can easily assay from about 100 to about 1500 different compounds. It is possible to assay several different plates per day; assay screens for up to about 6,000–20,000 different compounds are possible using the integrated systems of the invention. More recently, microfluidic approaches to reagent manipulation have been developed.

The molecule of interest can be bound to the solid state component, directly or indirectly, via covalent or non covalent linkage, e.g., via a tag. The tag can be any of a variety of components. In general, a molecule that binds the tag (a tag binder) is fixed to a solid support, and the tagged molecule of interest (e.g., Archipelin) is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.) Antibodies to molecules with natural binders such as biotin are also widely available and appropriate tag binders (see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody. In addition to antibody-antigen interactions, receptor-ligand interactions are also appropriate as tag and tag-binder pairs, such as agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherin family, the integrin family, the selectin family, and the like; see, e.g., Pigott & Power, *The Adhesion Molecule Facts Book I* (1993)). Similarly, toxins and venoms, viral epitopes, hormones (e.g., opiates, steroids, etc.), intracellular receptors (e.g., which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly Gly sequences of between about 5 and 200 amino acids (SEQ ID NO:53). Such flexible linkers are known to those of skill in the art. For example, poly(ethylene glycol) linkers are available from Shearwater Polymers, Inc., Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature (see, e.g., Merrifield, *J. Am. Chem. Soc.* 85:2149–2154 (1963) (describing solid phase synthesis of, e.g., peptides); Geysen et al., *J. Immun. Meth.* 102: 259–274 (1987) (describing synthesis of solid phase components on pins); Frank and Doring, *Tetrahedron* 44:60316040 (1988) (describing synthesis of various peptide sequences on cellulose disks); Fodor et al., *Science,* 251:767–777 (1991); Sheldon et al., *Clinical Chemistry* 39(4):718–719 (1993); and Kozal et al., *Nature Medicine* 2(7):753759 (1996) (all describing arrays of biopolymers fixed to solid substrates). Non-chemical approaches for fixing tag binders to substrates include other common methods, such as heat, cross-linking by UV radiation, and the like.

The invention provides in vitro assays for identifying, in a high throughput format, compounds that can modulate the expression or activity of Archipelin. Control reactions that measure Archipelin activity of the cell in a reaction that does not include a potential modulator are optional, as the assays are highly uniform. Such optional control reactions are appropriate and increase the reliability of the assay. Accordingly, in some embodiments, the methods of the invention include such a control reaction. For each of the assay formats described, "no modulator" control reactions which do not include a modulator provide a background level of binding activity.

In some assays it will be desirable to have positive controls to ensure that the components of the assays are working properly. At least two types of positive controls are appropriate. First, a known activator of Archipelin of the invention can be incubated with one sample of the assay, and the resulting increase in signal resulting from an increased expression level or activity of Archipelin determined according to the methods herein. Second, a known inhibitor of Archipelin can be added, and the resulting decrease in signal for the expression or activity of Archipelin can be similarly detected. It will be appreciated that modulators can also be combined with activators or inhibitors to find modulators which inhibit the increase or decrease that is otherwise caused by the presence of the known modulator of Archipelin.

D. Computer-Based Assays

Yet another assay for compounds that modulate the activity of Archipelin involves computer assisted drug design, in which a computer system is used to generate a three-dimensional structure of Archipelin based on the structural information encoded by its amino acid sequence. The input amino acid sequence interacts directly and actively with a pre-established algorithm in a computer program to yield secondary, tertiary, and quaternary structural models of the protein. Similar analyses can be performed on potential receptors of Archipelin. The models of the protein structure are then examined to identify regions of the structure that have the ability to bind, e.g., Archipelin. These regions are then used to identify polypeptides that bind to Archipelin.

The three-dimensional structural model of the protein is generated by entering protein amino acid sequences of at least 10 amino acid residues or corresponding nucleic acid sequences encoding a potential Archipelin receptor into the computer system. The amino acid sequences encoded by the nucleic acid sequences provided herein represent the primary sequences or subsequences of the proteins, which encode the structural information of the proteins. At least 10 residues of an amino acid sequence (or a nucleotide sequence encoding 10 amino acids) are entered into the computer system from computer keyboards, computer readable substrates that include, but are not limited to, electronic storage media (e.g., magnetic diskettes, tapes, cartridges, and chips), optical media (e.g., CD ROM), information distributed by internet sites, and by RAM. The three-dimensional structural model of the protein is then generated by the interaction of the amino acid sequence and the computer system, using software known to those of skill in the art.

The amino acid sequence represents a primary structure that encodes the information necessary to form the secondary, tertiary and quaternary structure of the protein of interest. The software looks at certain parameters encoded by the primary sequence to generate the structural model. These parameters are referred to as "energy terms," and primarily include electrostatic potentials, hydrophobic potentials, solvent accessible surfaces, and hydrogen bonding. Secondary energy terms include van der Waals potentials. Biological molecules form the structures that minimize the energy terms in a cumulative fashion. The computer program is therefore using these terms encoded by the primary structure or amino acid sequence to create the secondary structural model.

The tertiary structure of the protein encoded by the secondary structure is then formed on the basis of the energy terms of the secondary structure. The user at this point can enter additional variables such as whether the protein is membrane bound or soluble, its location in the body, and its cellular location, e.g., cytoplasmic, surface, or nuclear. These variables along with the energy terms of the secondary structure are used to form the model of the tertiary structure. In modeling the tertiary structure, the computer program matches hydrophobic faces of secondary structure with like, and hydrophilic faces of secondary structure with like.

Once the structure has been generated, potential ligand binding regions are identified by the computer system. Three-dimensional structures for potential ligands are generated by entering amino acid or nucleotide sequences or chemical formulas of compounds, as described above. The three-dimensional structure of the potential ligand is then compared to that of Archipelin to identify binding sites of Archipelin. Binding affinity between the protein and ligands is determined using energy terms to determine which ligands have an enhanced probability of binding to the protein.

Computer systems are also used to screen for mutations, polymorphic variants, alleles and interspecies homologs of genes encoding an Archipelin polypeptide of the invention. Such mutations can be associated with disease states or genetic traits. As described above, GeneChip™ and related technology can also be used to screen for mutations, polymorphic variants, alleles and interspecies homologs. Once the variants are identified, diagnostic assays can be used to identify patients having such mutated genes. Identification of the mutated Archipelin genes involves receiving input of a first amino acid sequence of a Archipelin (or of a first nucleic acid sequence encoding a Archipelin of the invention), e.g., any amino acid sequence having at least 60%, optionally at least 85%, identity with the amino acid sequence of the polypeptide encoded by the nucleic acid sequence set forth in SEQ ID NO:1, SEQ ID NO:3, SEQ ID NO:5, and SEQ ID NO:8, or conservatively modified versions thereof. The sequence is entered into the computer system as described above. The first nucleic acid or amino acid sequence is then compared to a second nucleic acid or amino acid sequence that has substantial identity to the first sequence. The second sequence is entered into the computer system in the manner described above. Once the first and second sequences are compared, nucleotide or amino acid differences between the sequences are identified. Such sequences can represent allelic differences in various Archipelin genes, and mutations associated with disease states and genetic traits.

VII. Compositions, Kits and Integrated Systems

The invention provides compositions, kits and integrated systems for practicing the assays described herein using nucleic acids encoding the Archipelin polypeptides of the invention, or Archipelin proteins, anti-Archipelin antibodies, etc.

The invention provides assay compositions for use in solid phase assays; such compositions can include, for example, one or more nucleic acids encoding an Archipelin immobilized on a solid support, and a labeling reagent. In each case, the assay compositions can also include additional reagents that are desirable for hybridization. Modulators of expression or activity of an Archipelin of the invention can also be included in the assay compositions. Solid supports include, e.g., petri plates, microtiter dishes and microarrays.

The invention also provides kits for carrying out the assays of the invention. The kits typically include a probe which comprises an antibody that specifically binds to Archipelin or a polynucleotide sequence encoding an Archipelin polypeptide, and a label for detecting the presence of the probe. The kits may include several polynucleotide sequences encoding Archipelin polypeptides of the invention. Kits can include any of the compositions noted above, and optionally further include additional components such as instructions to practice a high-throughput method of assaying for an effect on expression of the genes encoding the Archipelin polypeptides of the invention, or on activity of the Archipelin polypeptides of the invention, one or more containers or compartments (e.g., to hold the probe, labels, or the like), a control modulator of the expression or activity of Archipelin polypeptides, a robotic armature for mixing kit components or the like.

The invention also provides integrated systems for high-throughput screening of potential modulators for an effect on the expression or activity of the Archipelin polypeptides of the invention. The systems typically include a robotic armature which transfers fluid from a source to a destination, a controller which controls the robotic armature, a label detector, a data storage unit which records label detection, and an assay component such as a microtiter dish comprising a well having a reaction mixture or a substrate comprising a fixed nucleic acid or immobilization moiety.

A number of robotic fluid transfer systems are available, or can easily be made from existing components. For example, a Zymate XP (Zymark Corporation; Hopkinton, Mass.) automated robot using a Microlab 2200 (Hamilton; Reno, Nev.) pipetting station can be used to transfer parallel samples to 96 well microtiter plates to set up several parallel simultaneous binding assays.

Optical images viewed (and, optionally, recorded) by a camera or other recording device (e.g., a photodiode and data storage device) are optionally further processed in any of the embodiments herein, e.g., by digitizing the image and storing and analyzing the image on a computer. A variety of commercially available peripheral equipment and software is available for digitizing, storing and analyzing a digitized video or digitized optical image, e.g., using PC (Intel x86 or Pentium chip-compatible DOS®, OS2® WINDOWS®, WINDOWS NT® or WINDOWS95® based computers), MACINTOSH®, or UNIX® based (e.g., SUN® work station) computers.

One conventional system carries light from the specimen field to a cooled charge-coupled device (CCD) camera, in common use in the art. A CCD camera includes an array of picture elements (pixels). The light from the specimen is imaged on the CCD. Particular pixels corresponding to regions of the specimen (e.g., individual hybridization sites on an array of biological polymers) are sampled to obtain light intensity readings for each position. Multiple pixels are processed in parallel to increase speed. The apparatus and methods of the invention are easily used for viewing any sample, e.g., by fluorescent or dark field microscopic techniques.

VIII. Gene Therapy Applications

A variety of human diseases can be treated by therapeutic approaches that involve stably introducing a gene into a human cell such that the gene is transcribed and the gene product is produced in the cell. Diseases amenable to treatment by this approach include inherited diseases, including those in which the defect is in a single gene. Gene therapy is also useful for treatment of acquired diseases and other conditions. For discussions on the application of gene therapy towards the treatment of genetic as well as acquired diseases, see, Miller *Nature* 357:455–460 (1992); and Mulligan *Science* 260:926–932 (1993).

In the context of the present invention, gene therapy can be used for treating a variety of disorders and/or diseases in which Archipelin has been implicated. For example, introduction by gene therapy of polynucleotides encoding an Archipelin polypeptide of the invention can be used to treat, e.g., diabetes.

A. Vectors for Gene Delivery

For delivery to a cell or organism, the nucleic acids of the invention can be incorporated into a vector. Examples of vectors used for such purposes include expression plasmids capable of directing the expression of the nucleic acids in the target cell. In other instances, the vector is a viral vector system wherein the nucleic acids are incorporated into a viral genome that is capable of transfecting the target cell. In embodiments, the nucleic acids can be operably linked to expression and control sequences that can direct expression of the gene in the desired target host cells. Thus, one can achieve expression of the nucleic acid under appropriate conditions in the target cell.

B. Gene Delivery Systems

Viral vector systems useful in the expression of the nucleic acids include, for example, naturally occurring or recombinant viral vector systems. Depending upon the particular application, suitable viral vectors include replication competent, replication deficient, and conditionally replicating viral vectors. For example, viral vectors can be derived from the genome of human or bovine adenoviruses, vaccinia virus, herpes virus, adeno-associated virus, minute virus of mice (MVM), HIV, sindbis virus, and retroviruses (including but not limited to Rous sarcoma virus), and MoMLV. Typically, the genes of interest are inserted into such vectors to allow packaging of the gene construct, typically with accompanying viral DNA, followed by infection of a sensitive host cell and expression of the gene of interest.

As used herein, "gene delivery system" refers to any means for the delivery of a nucleic acid of the invention to a target cell. In some embodiments of the invention, nucleic acids are conjugated to a cell receptor ligand for facilitated uptake (e.g., invagination of coated pits and internalization of the endosome) through an appropriate linking moiety, such as a DNA linking moiety (Wu et al., *J. Biol. Chem.* 263:14621–14624 (1988); WO 92/06180). For example, nucleic acids can be linked through a polylysine moiety to asialo-oromucocid, which is a ligand for the asialoglycoprotein receptor of hepatocytes.

Similarly, viral envelopes used for packaging gene constructs that include the nucleic acids of the invention can be modified by the addition of receptor ligands or antibodies specific for a receptor to permit receptor-mediated endocytosis into specific cells (see, e.g., WO 93/20221, WO 93/14188, and WO 94/06923). In some embodiments of the invention, the DNA constructs of the invention are linked to viral proteins, such as adenovirus particles, to facilitate endocytosis (Curiel et al., *Proc. Natl. Acad. Sci. U.S.A.* 88:8850–8854 (1991)). In other embodiments, molecular conjugates of the instant invention can include microtubule inhibitors (WO/9406922), synthetic peptides mimicking influenza virus hemagglutinin (Plank et al., *J. Biol. Chem.* 269:12918–12924 (1994)), and nuclear localization signals such as SV40 T antigen (WO93/19768).

Retroviral vectors are also useful for introducing the nucleic acids of the invention into target cells or organisms. Retroviral vectors are produced by genetically manipulating retroviruses. The viral genome of retroviruses is RNA. Upon infection, this genomic RNA is reverse transcribed into a DNA copy which is integrated into the chromosomal DNA of transduced cells with a high degree of stability and efficiency. The integrated DNA copy is referred to as a provirus and is inherited by daughter cells as is any other gene. The wild type retroviral genome and the proviral DNA have three genes: the gag, the pol and the env genes, which are flanked by two long terminal repeat (LTR) sequences. The gag gene encodes the internal structural (nucleocapsid) proteins; the pol gene encodes the RNA directed DNA polymerase (reverse transcriptase); and the env gene encodes viral envelope glycoproteins. The 5' and 3' LTRs serve to promote transcription and polyadenylation of virion RNAs. Adjacent to the 5' LTR are sequences necessary for reverse transcription of the genome (the tRNA primer binding site) and for efficient encapsulation of viral RNA into particles (the Psi site) (see, Mulligan, In: *Experimental Manipulation of Gene Expression*, Inouye (ed), 155–173 (1983); Mann et al., *Cell* 33:153–159 (1983); Cone and Mulligan, *Proceedings of the National Academy of Sciences, U.S.A.*, 81:6349–6353 (1984)).

The design of retroviral vectors is well known to those of ordinary skill in the art. In brief, if the sequences necessary for encapsidation (or packaging of retroviral RNA into infectious virions) are missing from the viral genome, the result is a cis acting defect which prevents encapsidation of genomic RNA. However, the resulting mutant is still capable of directing the synthesis of all virion proteins. Retroviral genomes from which these sequences have been deleted, as well as cell lines containing the mutant genome stably integrated into the chromosome are well known in the art and are used to construct retroviral vectors. Preparation of retroviral vectors and their uses are described in many publications including, e.g., European Patent Application EPA 0 178 220; U.S. Pat. No. 4,405,712, Gilboa *Biotechniques* 4:504–512 (1986); Mann et al., *Cell* 33:153–159 (1983); Cone and Mulligan *Proc. Natl. Acad. Sci. USA* 81:6349–6353 (1984); Eglitis et al. *Biotechniques* 6:608–614 (1988); Miller et al. *Biotechniques* 7:981–990 (1989); Miller (1992) supra; Mulligan (1993), supra; and WO 92/07943.

The retroviral vector particles are prepared by recombinantly inserting the desired nucleotide sequence into a retrovirus vector and packaging the vector with retroviral capsid proteins by use of a packaging cell line. The resultant retroviral vector particle is incapable of replication in the host cell but is capable of integrating into the host cell genome as a proviral sequence containing the desired nucleotide sequence. As a result, the patient is capable of producing, for example, an Archipelin polypeptide of interest and thus restore the cells to a normal phenotype.

Packaging cell lines that are used to prepare the retroviral vector particles are typically recombinant mammalian tissue culture cell lines that produce the necessary viral structural proteins required for packaging, but which are incapable of producing infectious virions. The defective retroviral vectors that are used, on the other hand, lack these structural genes but encode the remaining proteins necessary for packaging. To prepare a packaging cell line, one can construct an infectious clone of a desired retrovirus in which the packaging site has been deleted. Cells comprising this construct will express all structural viral proteins, but the introduced DNA will be incapable of being packaged. Alternatively, packaging cell lines can be produced by transforming a cell line with one or more expression plasmids encoding the appropriate core and envelope proteins. In these cells, the gag, pol, and env genes can be derived from the same or different retroviruses.

A number of packaging cell lines suitable for the present invention are also available in the prior art. Examples of these cell lines include Crip, GPE86, PA317 and PG13 (see Miller et al., *J. Virol.* 65:2220–2224 (1991)). Examples of other packaging cell lines are described in Cone and Mulligan *Proceedings of the National Academy of Sciences, USA*, 81:6349–6353 (1984); Danos and Mulligan *Proceedings of the National Academy of Sciences, USA*, 85:6460–6464 (1988); Eglitis et al. (1988), supra; and Miller (1990), supra.

Packaging cell lines capable of producing retroviral vector particles with chimeric envelope proteins may be used. Alternatively, amphotropic or xenotropic envelope proteins, such as those produced by PA317 and GPX packaging cell lines may be used to package the retroviral vectors.

In some embodiments of the invention, an antisense nucleic acid is administered which hybridizes to a gene encoding an Archipelin of the invention or to a transcript thereof. The antisense nucleic acid can be provided as an antisense oligonucleotide (see, e.g., Murayama et al., *Antisense Nucleic Acid Drug Dev.* 7:109–114 (1997)). Genes encoding an antisense nucleic acid can also be provided; such genes can be introduced into cells by methods known to those of skill in the art. For example, one can introduce a gene that encodes an antisense nucleic acid in a viral vector, such as, for example, in hepatitis B virus (see, e.g., Ji et al., *J. Viral Hepat.* 4:167–173 (1997)), in adeno-associated virus (see, e.g., Xiao et al., *Brain Res.* 756:76–83 (1997)), or in other systems including, but not limited, to an HVJ (Sendai virus)-liposome gene delivery system (see, e.g., Kaneda et al., *Ann. NY Acad. Sci.* 811:299–308 (1997)), a "peptide vector" (see, e.g., Vidal et al., *CR Acad. Sci III* 32:279–287 (1997)), as a gene in an episomal or plasmid vector (see, e.g., Cooper et al., *Proc. Natl. Acad. Sci. U.S.A.* 94:6450–6455 (1997), Yew et al. *Hum Gene Ther.* 8:575–584 (1997)), as a gene in a peptide-DNA aggregate (see, e.g., Niidome et al., *J. Biol. Chem.* 272:15307–15312 (1997)), as "naked DNA" (see, e.g., U.S. Pat. Nos. 5,580,859 and 5,589,466), in lipidic vector systems (see, e.g., Lee et al., *Crit Rev Ther Drug Carrier Syst.* 14:173–206 (1997)), polymer coated liposomes (U.S. Pat. Nos. 5,213,804 and 5,013,556), cationic liposomes (Epand et al., U.S. Pat. Nos. 5,283,185; 5,578,475; 5,279,833; and 5,334,761), gas filled microspheres (U.S. Pat. No. 5,542,935), ligand-targeted encapsulated macromolecules (U.S. Pat. Nos. 5,108,921; 5,521,291; 5,554,386; and 5,166,320).

C. Pharmaceutical Formulations

When used for pharmaceutical purposes, the vectors used for gene therapy are formulated in a suitable buffer, which can be any pharmaceutically acceptable buffer, such as phosphate buffered saline or sodium phosphate/sodium sulfate, Tris buffer, glycine buffer, sterile water, and other buffers known to the ordinarily skilled artisan such as those described by Good et al. *Biochemistry* 5:467 (1966).

The compositions can additionally include a stabilizer, enhancer or other pharmaceutically acceptable carriers or vehicles. A pharmaceutically acceptable carrier can contain a physiologically acceptable compound that acts, for example, to stabilize the nucleic acids of the invention and any associated vector. A physiologically acceptable compound can include, for example, carbohydrates, such as glucose, sucrose or dextrans, antioxidants, such as ascorbic acid or glutathione, chelating agents, low molecular weight proteins or other stabilizers or excipients. Other physiologically acceptable compounds include wetting agents, emulsifying agents, dispersing agents or preservatives, which are particularly useful for preventing the growth or action of microorganisms. Various preservatives are well known and include, for example, phenol and ascorbic acid. Examples of carriers, stabilizers or adjuvants can be found in Remington's *Pharmaceutical Sciences*, Mack Publishing Company, Philadelphia, Pa., 17th ed. (1985).

D. Administration of Formulations

The formulations of the invention can be delivered to any tissue or organ using any delivery method known to the ordinarily skilled artisan. In some embodiments of the invention, the nucleic acids of the invention are formulated in mucosal, topical, and/or buccal formulations, particularly mucoadhesive gel and topical gel formulations. Exemplary permeation enhancing compositions, polymer matrices, and mucoadhesive gel preparations for transdermal delivery are disclosed in U.S. Pat. No. 5,346,701.

E. Methods of Treatment

The gene therapy formulations of the invention are typically administered to a cell. The cell can be provided as part of a tissue, such as an epithelial membrane, or as an isolated cell, such as in tissue culture. The cell can be provided in vivo, ex vivo, or in vitro.

The formulations can be introduced into the tissue of interest in vivo or ex vivo by a variety of methods. In some embodiments of the invention, the nucleic acids of the invention are introduced into cells by such methods as microinjection, calcium phosphate precipitation, liposome fusion, or biolistics. In further embodiments, the nucleic acids are taken up directly by the tissue of interest.

In some embodiments of the invention, the nucleic acids of the invention are administered ex vivo to cells or tissues explanted from a patient, then returned to the patient. Examples of ex vivo administration of therapeutic gene constructs include Nolta et al., *Proc Natl. Acad. Sci. USA* 93(6):2414–9 (1996); Koc et al., *Seminars in Oncology* 23 (1):46–65 (1996); Raper et al., *Annals of Surgery* 223(2): 116–26 (1996); Dalesandro et al., *J. Thorac. Cardi. Surg.*, 11(2):416–22 (1996); and Makarov et al., *Proc. Natl. Acad. Sci. USA* 93(1):402–6 (1996).

IX. Administration and Pharmaceutical Compositions

Modulators of Archipelin (e.g., agonists, including Archipelin polypeptides, and antagonists) can be administered directly to the mammalian subject for modulation of Archipelin signaling in vivo. Administration is by any of the routes normally used for introducing a modulator compound into ultimate contact with the tissue to be treated and well known to those of skill in the art. Although more than one route can be used to administer a particular composition, a particular route can often provide a more immediate and more effective reaction than another route.

The compounds of the present invention can also be used effectively in combination with one or more additional active agents depending on the desired target therapy (see, e.g., Turner, N. et al. *Prog. Drug Res.* (1998) 51: 33–94; Haffner, S. *Diabetes Care* (1998) 21: 160–178; and DeFronzo, R. et al. (eds.), *Diabetes Reviews* (1997) Vol. 5 No. 4). A number of studies have investigated the benefits of combination therapies with oral agents (see, e.g., Mahler, R., *J. Clin. Endocrinol. Metab.* (1999) 84: 1165–71; United Kingdom Prospective Diabetes Study Group: UKPDS 28, *Diabetes Care* (1998) 21: 87–92; Bardin, C. W., (ed.), *Current Therapy In Endocrinology And Metabolism*, 6th Edition (Mosby—Year Book, Inc., St. Louis, Mo. 1997); Chiasson, J. et al., *Ann. Intern. Med.* (1994) 121: 928–935; Coniff, R. et al., *Clin. Ther.* (1997) 19: 16–26; Coniff, R. et al., *Am. J. Med.* (1995) 98: 443–451; and Iwamoto, Y. et al., *Diabet. Med.* (1996) 13 365–370; Kwiterovich, P. *Am. J. Cardiol* (1998) 82(12A): 3U–17U). These studies indicate that modulation of diabetes and hyperlipidemia, among other diseases, can be further improved by the addition of a second agent to the therapeutic regimen. Combination therapy includes administration of a single pharmaceutical dosage formulation which contains an Archipelin modulator of the invention and one or more additional active agents, as well as administration of an Archipelin modulator and each active agent in its own separate pharmaceutical dosage formulation. For example, an Archipelin modulator and a thiazolidinedione can be administered to the human subject together in a single oral dosage composition, such as a tablet or capsule, or each agent can be administered in separate oral dosage formulations. Where separate dosage formulations are used, an Archipelin modulator and one or more additional active agents can be administered at essentially the same time (i.e., concurrently), or at separately staggered times (i.e., sequentially). Combination therapy is understood to include all these regimens.

Still another example of combination therapy can be seen in modulating diabetes (or treating diabetes and its related symptoms, complications, and disorders), wherein the AKRIC modulators can be effectively used in combination with, for example, sulfonylureas (such as chlorpropamide, tolbutamide, acetohexamide, tolazamide, glyburide, gliclazide, glynase, glimepiride, and glipizide), biguanides (such as metformin), a PPAR beta delta agonist, a ligand or agonist of PPAR alpha such as thiazolidinediones (such as ciglitazone, pioglitazone (see, e.g., U.S. Pat. No. 6,218,409), troglitazone, and rosiglitazone (see, e.g., U.S. Pat. No. 5,859,037)); dehydroepiandrosterone (also referred to as DHEA or its conjugated sulphate ester, DHEA-SO4); antiglucocorticoids; TNFα inhibitors; α-glucosidase inhibitors (such as acarbose, miglitol, and voglibose), amylin and amylin derivatives (such as pramlintide, (see, also, U.S. Pat. Nos. 5,902,726; 5,124,314; 5,175,145 and 6,143,718, 6,136, 784)), insulin secretogogues (such as repaglinide, gliquidone, and nateglinide (see, also, U.S. Pat. Nos. 6,251,856; 6,251,865; 6,221,633; 6,174,856)), insulin, as well as the active agents discussed above for treating atherosclerosis.

The pharmaceutical compositions of the invention may comprise a pharmaceutically acceptable carrier. Pharmaceutically acceptable carriers are determined in part by the particular composition being administered, as well as by the particular method used to administer the composition. Accordingly, there is a wide variety of suitable formulations of pharmaceutical compositions of the present invention (see, e.g., *Remington's Pharmaceutical Sciences*, 17$^{th}$ ed. 1985)).

The modulators (e.g., agonists or antagonists) of the expression or activity of the Archipelin, alone or in combination with other suitable components, can be prepared for injection or for use in a pump device. Pump devices (also known as "insulin pumps") are commonly used to administer insulin to patients and therefore can be easily adapted to include compositions of the present invention. Manufacturers of insulin pumps include Animas, Disetronic and .MiniMed.

The modulators (e.g., agonists or antagonists) of the expression or activity of the Archipelin, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for administration include aqueous and non-aqueous solutions, isotonic sterile solutions, which can contain antioxidants, buffers, bacteriostats, and solutes that render the formulation isotonic, and aqueous and non-aqueous sterile suspensions that can include suspending agents, solubilizers, thickening agents, stabilizers, and preservatives. In the practice of this invention, compositions can be administered, for example, orally, nasally, topically, intravenously, intraperitoneally, or intrathecally. The formulations of compounds can be presented in unit-dose or multi-dose sealed containers, such as ampoules and vials. Solutions and suspensions can be prepared from sterile powders, granules, and tablets of the kind previously described. The modulators can also be administered as part a of prepared food or drug.

The dose administered to a patient, in the context of the present invention should be sufficient to effect a beneficial response in the subject over time. The optimal dose level for any patient will depend on a variety of factors including the efficacy of the specific modulator employed, the age, body weight, physical activity, and diet of the patient, on a possible combination with other drugs, and on the severity of the case of diabetes. It is recommended that the daily dosage of the modulator be determined for each individual patient by those skilled in the art in a similar way as for known insulin compositions. The size of the dose also will be determined by the existence, nature, and extent of any adverse side-effects that accompany the administration of a particular compound or vector in a particular subject.

In determining the effective amount of the modulator to be administered a physician may evaluate circulating plasma levels of the modulator, modulator toxicity, and the production of anti-modulator antibodies. In general, the dose equivalent of a modulator is from about 1 ng/kg to 10 mg/kg for a typical subject.

For administration, Archipelin modulators of the present invention can be administered at a rate determined by the LD-50 of the modulator, and the side-effects of the inhibitor at various concentrations, as applied to the mass and overall health of the subject. Administration can be accomplished via single or divided doses.

X. Diagnosis of Diabetes

The present invention also provides methods of diagnosing diabetes or a predisposition of at least some of the pathologies of diabetes. Diagnosis involves determining the level of Archipelin in a patient and then comparing the level to a baseline or range. Typically, the baseline value is representative of Archipelin in a healthy (i.e., non-diabetic) person. As discussed above, variation of levels (either high or low) of Archipelin from the baseline range suggests that the patient is either diabetic or at risk of developing at least some of the pathologies of diabetes. Variation van be, e.g., at least 5%, 10%, 20%, 50%, 200%, 400%, 500%, or 1000% or more of a baseline value or range. In some embodiments, the level of Archipelin are measured by taking a blood sample from a patient and measuring the amount of Archipelin in the sample using any number of detection methods, such as those discussed herein. For instance, fasting and fed blood or urine levels can be tested.

Glucose tolerance tests can also be used to detect the effect of glucose levels on Archipelin levels. In glucose tolerance tests, the patient's ability to tolerate a standard oral glucose load is evaluated by assessing serum and urine specimens for glucose levels. Blood samples are taken before the glucose is ingested, glucose is given by mouth, and blood or urine glucose levels are tested at set intervals after glucose ingestion.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

EXAMPLES

The following examples are offered to illustrate, but not to limit the claimed invention.

Example 1

This example describes the discovery of a new member of the CRF/urocortin family of peptides that is also highly abundant in pancreatic islets and is a hormone important for the treatment of diabetes mellitus.

Figure 2:
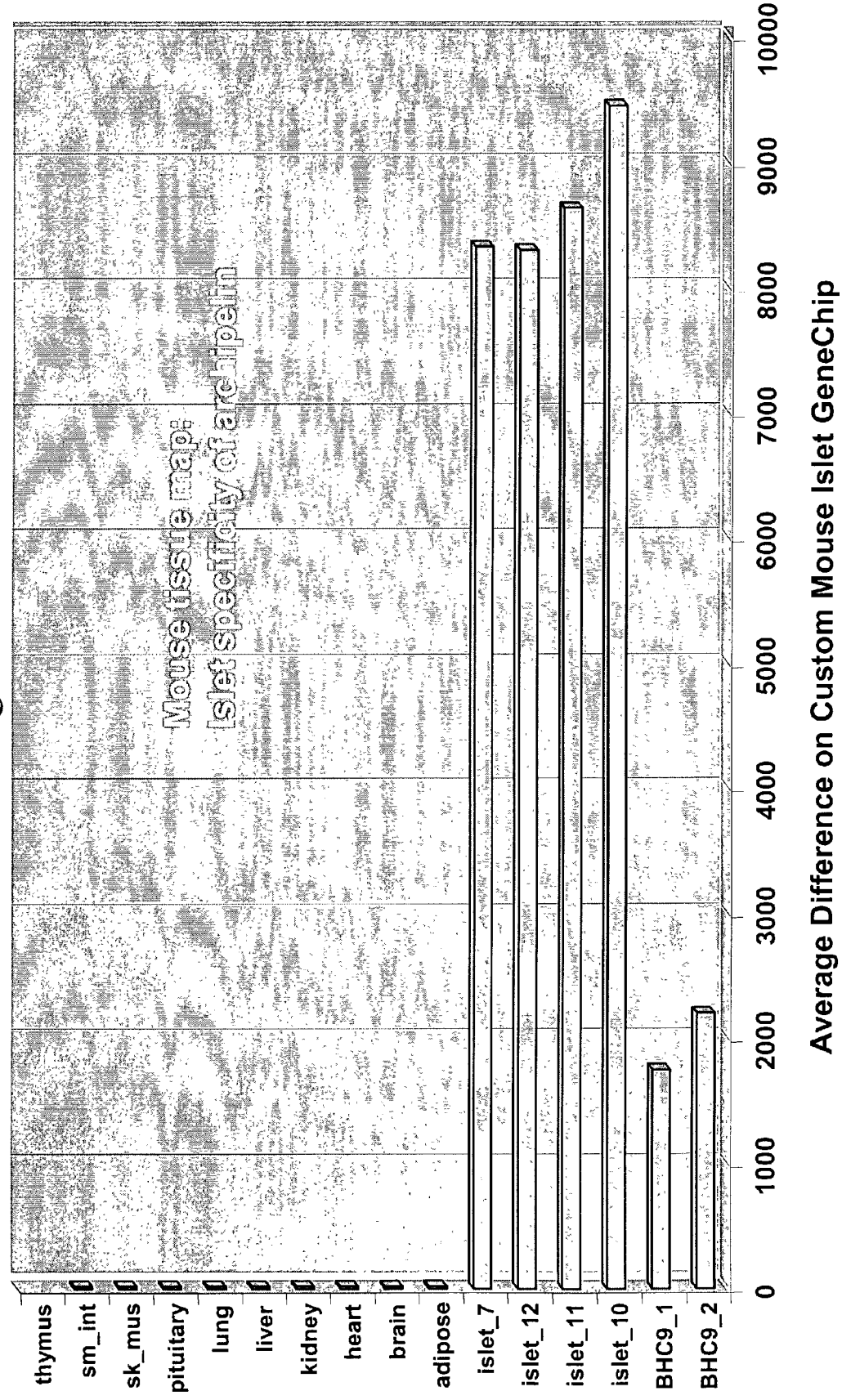
FIG. 2 illustrates the expression pattern of probe set MBXRATISL12276 in various tissues of mouse.

The probe set MBXRATISL12276 was identified as a gene specifically expressed in rat islets using rat tissue map experiments on rat islet GeneChips. Analysis of a second, more extensive, rat tissue mapping experiment also revealed that probe set MBXRATISL12276 was abundant in rat islet samples and absent in 10 samples from 10 other tissues. This probe set was present in 5 out of 5 rat islet samples with an average Average Difference of >4000 and was absent in all 10 other tissues with an average Average Difference value of 0 or less. This represents an extremely islet specific expression pattern. See FIG. 1. A mouse tissue map experiment also showed an extremely islet specific expression pattern. See FIG. 2. The predicted product of the gene corresponding to these probe sets was designated Archipelin.

Expression of Archipelin in diabetic animal models was also determined. This data indicated that probe set MBXRATISL12276 expression is 3-fold lower in Zucker Diabetic Fatty male rats versus ZLC control rats. This probe set is also lower in diabetic (fat fed) ZDF female rats. This data indicates that this gene is down-regulated in the islets of these animal models of Type 2 diabetes. These findings indicate that pancreatic islets are the major site of Archipelin production and suggests that this hormone is inappropriately expressed in individuals with diabetes mellitus. Type 1 diabetes is characterized by destruction of islets, and this will very likely lead to Archipelin levels to be reduced or absent. Islet disfunction is also a critical aspect of Type 2 diabetes and therefore also effects Archipelin production.

The nucleotide sequence of the mouse, rat and human Archipelin clones were determined. SEQ ID NO:1 and SEQ ID NO:8 display two variants of the human sequence, SEQ ID NO:3 shows the mouse sequence and SEQ ID NO:5 shows the rat sequence. The predicted amino acid sequences of unprocessed Archipelin are shown for human (SEQ ID NOs:2 and 7), mouse (SEQ ID NO:4) and rat (SEQ ID NO:6). Depending on the human clone sequenced, amino acid 94 was either arginine or glycine. Multiple clones encoded each amino acid.

Using MBXRATISL12276 to BLAST search a human islet endocrine cell database revealed ortholog clones among the human islet ESTs. cDNA clones for Archipelin were also abundant in the mouse and rat islet est databases. Subsequent Northern blot hybridizations with both rat and human cDNA clones of Archipelin confirm the islet specific expression of an approximately 1.2 kb Archipelin transcript.

A BLAST search of the public databases revealed significant similarity to swissprot+ database entry Q9i8e5 (*fugu rubripes* (japanese pufferfish) (*takifugu rubripes*)), which was designated as the *fugu* urocortin precursor. Further alignments suggested that the Archipelin peptide was also related to Corticotropin Releasing Factor (CRF) family. CRF is a key regulatory component of the hypothalamus-pituitary-adrenal axis. See, FIG. 3 illustrating an alignment of Archipelin amino acid sequences with members of the CRF peptide family. In light of the sequence analysis, it was determined that the Archipelin peptide was a processed, secreted peptide. FIGS. 3–5 illustrate the possible processing sites of the human, mouse and rat Archipelin peptides, respectively.

As noted above, the predicted Archipelin peptide sequence has a CRF family signature as well as a C-terminal proteolytic processing sequence (glycine-basic-basic-basic) that is characteristic for this family and results in C-terminal amidation. In the case of Archipelin from mouse, rat and human, this will result in an isoleucyl-amide. There are also basic residues in the region that is expected to be an N-terminal processing site (FIGS. 4–6) producing a mature peptide containing between 50 and 38 amino acid residues. More than one of these may exist physiologically and one or all of these may be biologically active. It is also possible that a larger version containing some or all of the propeptide has biological function.

A predicted mature peptide sequence for rat Archipelin (TKFTLSLDVPTNIMNILFNIDKAKNLRA-KAAANAQLMAQI-CONH2; SEQ ID NO:41) was obtained and used in a variety of biological studies. Without intending to limit the scope of the invention, it is predicted that this peptide represents a likely mature, processed version of the peptide.

In addition, the peptide sequence Cys-LFNIDKAKNL-RAK (SEQ ID NO:54), which represents residues 137 to 149 of the coding sequence of both rat and mouse Archipelin precursors was used to develop anti-sera. An affinity-purified version of this antibody recognizes the in vitro translated 160 amino acid rat Archipelin precursor molecule. This antiserum also recognizes the Archipelin precursor expressed by transfection of the rat Archipelin cDNA in HEK 293 cells on a western blot, as well as the 40-mer form of Archipelin (TKFTLSLDVPTNIMNILFNIDKAKNLRA-KAAANAQLMAQI-CONH2; SEQ ID NO:41).

Immunohistochemical studies using these antibodies demonstrated that Archipelin is highly expressed in islet cells, and in particular, in β-cells.

Moreover, in diabetes animal model systems, the animals typically displayed reduced levels of Archipelin their blood before a drop in insulin levels. These results indicate that monitoring Archipelin levels is particularly useful as an early indicator of a predisposition for diabetes.

Archipelin in Human Serum Samples

Figure 7:
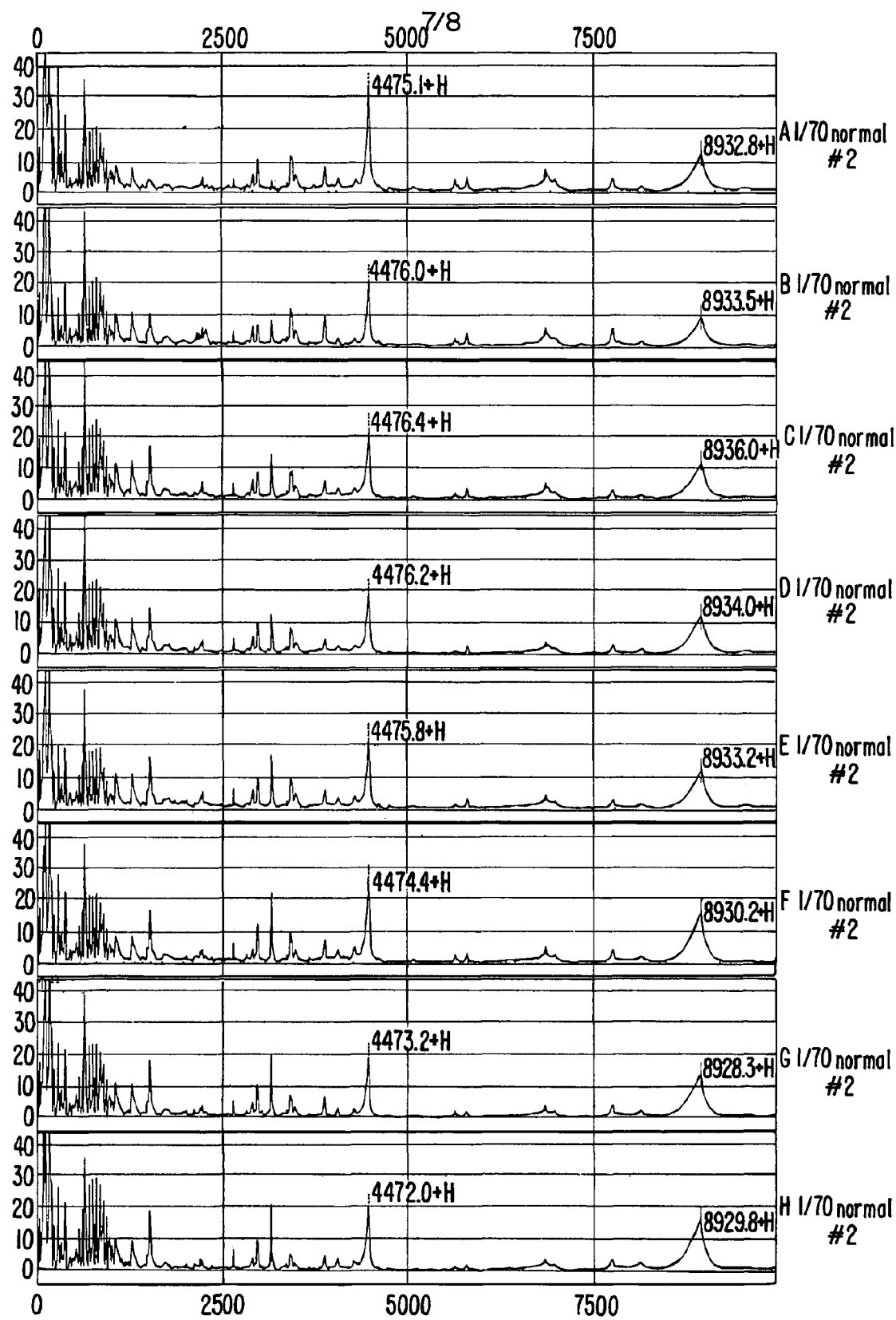
FIG. 7 illustrates detection of Archipelin in human serum using surface enhanced laser desorption ionization (SELDI) mass spectroscopy.

Human archipelin peptide was detected in normal human serum samples using surface enhanced laser desorption/ ionization (SELDI) mass spectroscopy of peptides specifically captured on a surface coated with affinity-purified anti-archipelin antibody (FIG. 7). This was accomplished using a Ciphergen protein chip reader instrument (Series PBS II). Affinity purified antibody was covalently bound to a PS20 pre-activated chip surface for the affinity capture of archipelin. Antibody was incubated on the chip surface overnight at 2–8° C. The 8 spot chip was then blocked for 30 minutes using a free amine from a 1M solution of ethanolamine. Dilutions (1:70) of human serum in PBS containing 0.05% Triton X were then applied to each of the spots and incubated for two hours at room temperature. Non-specific proteins were removed through post binding washes in PBS containing 0.05% triton-X. The energy-absorbing molecule CHCA was applied to the chip surface to form a crystal surface. Once crystal formation occurred the captured protein was ionized and read with the protein chip reader. The results revealed highly reproducible peaks at masses of 4472–4476 (monomer) and 8932–8936 (dimer). This size is consistent with the major serum form of the archipelin peptide being 40 or 41 amino acids (TKFTLSLD-VPTNIMNLLFNIAKAKNLRAQAAANAHLMAQI (SEQ ID NO:55) or RTKFTLSLDVPTNIMNLLFNIAKAKNL-RAQAAANAHLMAQI (SEQ ID NO:56)). (TKFTLSLD-VPTNIMNLLFNIAKAKNLRAQAAANAHLMAQI or RTKFTLSLDVPTNIMNLLFNIAKAKNL-RAQAAANAHLMAQI).

Trypsin Digestion Pattern of Rat Archipelin

Figure 8:
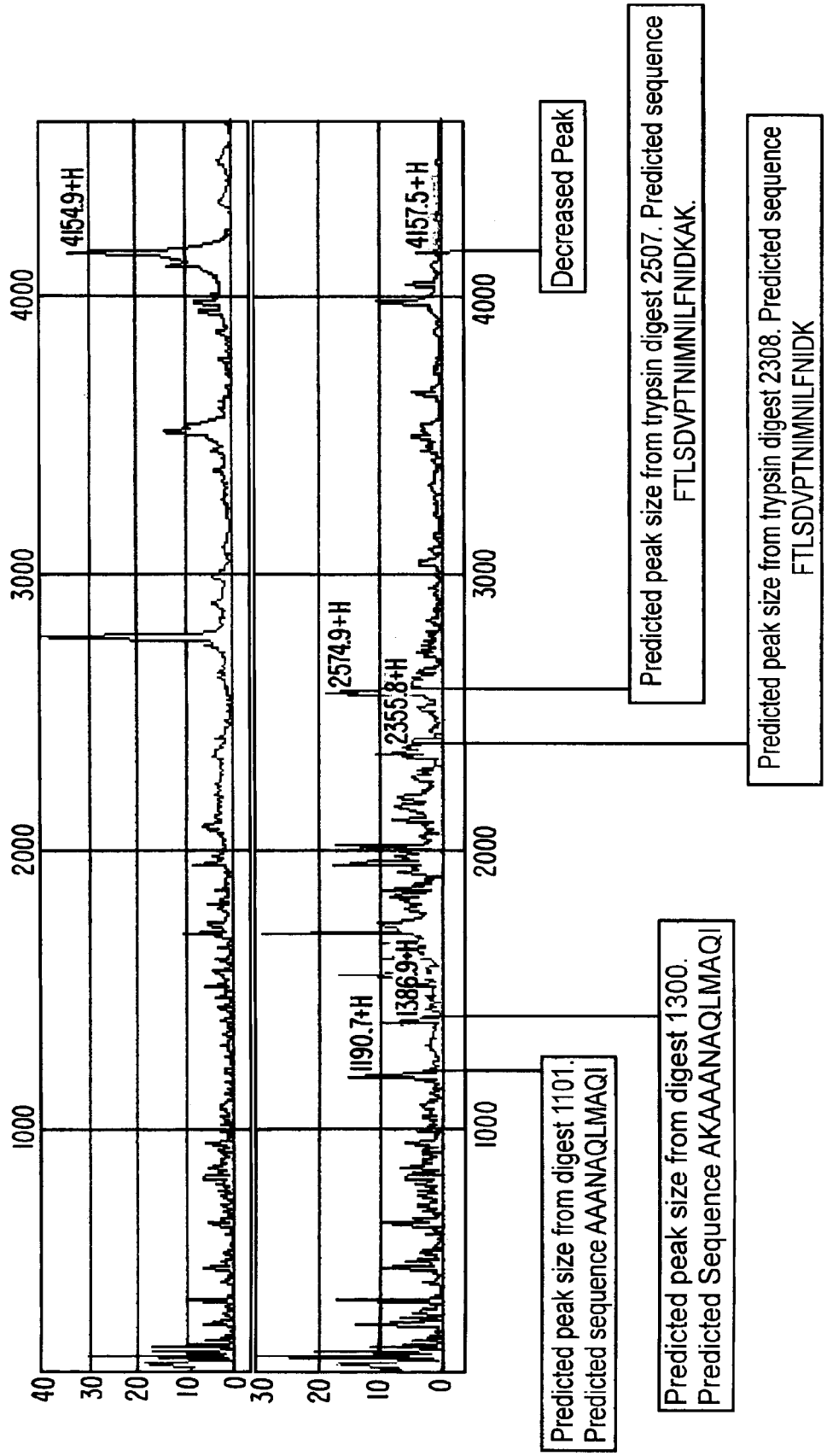
FIG. 8 illustrates detection of Archipelin (SEQ ID NOS: 49–52) in rat serum using surface enhanced laser desorption ionization (SELDI) mass spectroscopy.

After antibody capture of archipelin from rat serum using a PS 20 pre-activated Ciphergen chip, the peptide was digested using modified sequencing grade trypsin. Resulting peaks were identified based on predicted sequence from peptide cutter (expasy.org) (FIG. 8). The mass of the thirty-eight amino acid peptide of rat archipelin from rat was 4172 daltons. Capture of the native form of archipelin from serum was approximately 4150 daltons, which is within 0.5% of the expected mass. The major serum form of rat archipelin was therefore the 38-mer (FTLSLDVPTNIMNILFNID-KAKNLRAKAAANAQLMAQI; SEQ ID NO:57). Predicted trypsin digestion products closely matched the observed archipelin digestion.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of determining islet cell-specific activity in an individual, the method comprising,
    detecting the level of a polypeptide comprising SEQ ID NO:9 in a sample wherein the said sample comprises human blood from the individual, and
    determining islet cell-specific activity in the individual by comparing the level of the polypeptide in the sample to a baseline value or range associated with a known islet cell activity wherein said islet cell activity is associated with the ability of the islet cell to produce said polypeptide.

2. The method of claim 1, wherein the polypeptide comprises an amino acid sequence selected from the group consisting of SEQ ID NO:9, SEQ ID NO:10, SEQ ID NO:11, SEQ ID NO:12, SEQ ID NO:13, and SEQ ID NO:14.

3. The method of claim 1, wherein the polypeptide comprises SEQ ID NO:2.

4. The method of claim 1, wherein the polypeptide is detected by an antibody.

5. The method of claim 1, wherein the baseline or range is representative of the level of the polypeptide in a non-diabetic individual.

6. The method of claim 1, wherein the level of the polypeptide in the individual is altered compared to a level of the polypeptide in a non-diabetic individual.

7. The method of claim 6, wherein the level of the polypeptide in the individual is lower than a level of the polypeptide in a non-diabetic individual.

8. The method of claim 6, wherein the altered level of the polypeptide in the individual is higher than a level of the polypeptide in a non-diabetic individual.

9. The method of claim 6, wherein the level of the polypeptide in the individual is less than 50% of the level from the non-diabetic individual.

10. The method of claim 6, wherein the level of the polypeptide in the individual is at least 150% of the level from the non-diabetic individual.

* * * * *

SEQUENCE LISTING

<160> NUMBER OF SEQ ID NOS: 57

<210> SEQ ID NO 1
<211> LENGTH: 1080
<212> TYPE: DNA
<213> ORGANISM: Homo sapiens
<220> FEATURE:
<223> OTHER INFORMATION: human Archipelin A full-length cDNA
<220> FEATURE:
<221> NAME/KEY: modified_base
<222> LOCATION: (1)..(1080)
<223> OTHER INFORMATION: n = g, a, c or t

<400> SEQUENCE: 1

```
cacagcccac ttaggaacaa taccggagaa gcaggagccg agaccccgga gcagccacaa      60
gttcatgggg acgtgcacgg ggccgccctc ctggccctga agctgcgccg gcctccctga     120
gcgtttcgct gcggagggaa gtccactctc ggggagagat gctgatgccg gtccacttcc     180
tgctgctcct gctgctgctc ctgggggggcc ccaggacagg cctcccccac aagttctaca     240
aagccaagcc catcttcagc tgcctcaaca ccgccctgtc tgaggctgag aagggccagt     300
gggaggatgc atccctgctg agcaagagga gcttccacta cctgcgcagc agagacgcct     360
cttcgggaga ggaggaggag ggcaaagaga aaaagacttt ccccatctct ggggccaggg     420
gtggagccag aggcacccgg tacagatacg tgtcccaagc acagcccagg ggaaagccac     480
gccaggacac ggccaagagt ccccaccgca ccaagttcac cctgtccctc gacgtcccca     540
ccaacatcat gaacctcctc ttcaacatcg ccaaggccaa gaacctgcgt gcccaggcgg     600
ccgccaatgc ccacctgatg gcgcaaattg ggaggaagaa gtagaggcgg aggctggacg     660
ggagggcagc ggggtgngga gggggagggg aggggagggg gagggcnagg gggggagggg     720
aggggggaggg tgctgtctgc tggnttgtgt tttgtgggat cagtcagttt tacaggttgc     780
tgcactgctg agcccctctg atctcttctg gcctttgacc ctgtctccct cctgctctgt     840
ctgtacacac agaagtgcag tattgtccaa ccttcccaga cacaaagcag ctaacnttcc     900
tccctgtact caacgtctcc ttcctcccta cccacagcaa gaggcaaagt tcatgcattc     960
ctcctctcca gtcttctctc tgttgacccc atgcctgaga agagagcgtt cagggctcct    1020
ctcccacaca tcaacttctg ccagggcaga aagaggagct gcagcactcg ccttcctgac    1080
```

<210> SEQ ID NO 2
<211> LENGTH: 161
<212> TYPE: PRT
<213> ORGANISM: Homo sapiens
<220> FEATURE:
<223> OTHER INFORMATION: human unprocessed Archipelin A

<400> SEQUENCE: 2

```
Met Leu Met Pro Val His Phe Leu Leu Leu Leu Leu Leu Leu Leu Gly
 1               5                  10                  15

Gly Pro Arg Thr Gly Leu Pro His Lys Phe Tyr Lys Ala Lys Pro Ile
            20                  25                  30

Phe Ser Cys Leu Asn Thr Ala Leu Ser Glu Ala Glu Lys Gly Gln Trp
        35                  40                  45

Glu Asp Ala Ser Leu Leu Ser Lys Arg Ser Phe His Tyr Leu Arg Ser
    50                  55                  60

Arg Asp Ala Ser Ser Gly Glu Glu Glu Glu Gly Lys Glu Lys Lys Thr
65                  70                  75                  80
```

```
Phe Pro Ile Ser Gly Arg Gly Gly Ala Arg Gly Thr Arg Tyr Arg
                85                  90                  95
Tyr Val Ser Gln Ala Gln Pro Arg Gly Lys Pro Arg Gln Asp Thr Ala
                100                 105                 110
Lys Ser Pro His Arg Thr Lys Phe Thr Leu Ser Leu Asp Val Pro Thr
                115                 120                 125
Asn Ile Met Asn Leu Leu Phe Asn Ile Ala Lys Ala Lys Asn Leu Arg
            130                 135                 140
Ala Gln Ala Ala Ala Asn Ala His Leu Met Ala Gln Ile Gly Arg Lys
145                 150                 155                 160
Lys
```

<210> SEQ ID NO 3
<211> LENGTH: 1278
<212> TYPE: DNA
<213> ORGANISM: Mus sp.
<220> FEATURE:
<223> OTHER INFORMATION: mouse unprocessed Archipelin full-length cDNA

<400> SEQUENCE: 3

```
ggcacgaggc ttgtatttta aatgaaatct catcctaatg tagacactac atctggaatt      60
acgatccacc ctgtgatctg ccacttttac atatatgcac aggggagtgg agcggtttcc     120
atagagagga acgatcacag cccactacaa tcagtaccag agaagacaaa gctgcaaccc     180
tgaacagtca gaagttcaga ggacctgcag ggagtagcct cctggcccgg aagctgtgcc     240
cctcgacctg agcatttcca ctccagagca agtccacttt acaggagcg atgctgatgc     300
ccacctactt cctgctgcca cttctgctgc tcctaggagg tccaaggaca gcctctccc     360
acaagttcta caacactgga ccagtcttca gctgcctcaa cacagcccta tctgaggtca     420
agaagaacaa gctggaagat gtgcccttgc tgagcaagaa gagctttggc cacctgccca     480
cacaagaccc ctcaggggaa gaagatgaca ccaaacgca cctccagatc aaaagaactt     540
tctcaggtgc cgcgggtggg aatggagctg ggagcacccg gtacagatac aatcccagg     600
cacagcacaa ggggaagctg tacccagaca agcccaaaag cgaccggggc accaagttca     660
cccttttccct tgatgttccc actaacatca tgaacatcct cttcaacatc gacaaggcca     720
agaaatttgcg agccaaggca gctgccaatg ctcagctcat ggcacagatt gggaagaaga     780
agtaaagcaa agcccaggca tgagggtggc acatcaagac aagggccccg gagtaaaggg     840
taaaggaaac tgaggacgtg ccctcgaatt tcaaaggaca gtctgttttc ccaggctgct     900
ccactactgt gcccctctga tcctctcttg cttccagtcc ggtttccctt ctcagtacat     960
acacactcaa gcgcagtatt gctcagccca tatccacaat ggaggttaac gtctctcccc    1020
gaatcctgtg tctgctttct ggttccctgt aacaacagac aagttcatgt ggtgcccctc    1080
cttcccaagc cctccctgg tgtcaccatg tctgcagaga gagctttcag gctccctcct    1140
tgtcccacat tggtctgagc ctcggcagag acacagagat gcacagctcc cctcttgat    1200
accaaatacc tccctactt cctcatctgg attaaagtca gtggcttctt gaaaaaaaaa    1260
aaaaaaaaaa aaaaaaaa                                                 1278
```

<210> SEQ ID NO 4
<211> LENGTH: 164
<212> TYPE: PRT
<213> ORGANISM: Mus sp.
<220> FEATURE:
<223> OTHER INFORMATION: mouse unprocessed Archipelin

<400> SEQUENCE: 4

```
Met Leu Met Pro Thr Tyr Phe Leu Leu Pro Leu Leu Leu Leu Gly
1               5                   10                  15

Gly Pro Arg Thr Ser Leu Ser His Lys Phe Tyr Asn Thr Gly Pro Val
            20                  25                  30

Phe Ser Cys Leu Asn Thr Ala Leu Ser Glu Val Lys Lys Asn Lys Leu
        35                  40                  45

Glu Asp Val Pro Leu Leu Ser Lys Lys Ser Phe Gly His Leu Pro Thr
    50                  55                  60

Gln Asp Pro Ser Gly Glu Glu Asp Asn Gln Thr His Leu Gln Ile
65                  70                  75                  80

Lys Arg Thr Phe Ser Gly Ala Ala Gly Gly Asn Gly Ala Gly Ser Thr
                85                  90                  95

Arg Tyr Arg Tyr Gln Ser Gln Ala Gln His Lys Gly Lys Leu Tyr Pro
                100                 105                 110

Asp Lys Pro Lys Ser Asp Arg Gly Thr Lys Phe Thr Leu Ser Leu Asp
            115                 120                 125

Val Pro Thr Asn Ile Met Asn Ile Leu Phe Asn Ile Asp Lys Ala Lys
    130                 135                 140

Asn Leu Arg Ala Lys Ala Ala Asn Ala Gln Leu Met Ala Gln Ile
145                 150                 155                 160

Gly Lys Lys Lys
```

<210> SEQ ID NO 5
<211> LENGTH: 1186
<212> TYPE: DNA
<213> ORGANISM: Rattus sp.
<220> FEATURE:
<223> OTHER INFORMATION: rat Archipelin unprocessed full-length cDNA

<400> SEQUENCE: 5

```
ccggcgtgca cagctggctc tagttgtatt ttaaatgaaa tctcatccta agtagacac      60
tacgtctgga attacgatcc accctgtgat ctgtcacttt tacatacatg cacaggggag    120
tggagcggtt tccatagaga ggaactacca cagctcacta cgaacaatac cagagaagac    180
gaagctgcga ccccgaacaa gaggacctgc ggggagcagc cctccgggcc cagaagctgt    240
gcccctcgcc ctgagcactt ccaccctaga gcaaagtcct cttacagtac agggagcgat    300
gctgatgccc acttacttcc tgctgcttct gctgctgctc ctaggggccc aaggacaag    360
cctctcccac aagttctaca cgcaggacc aatcttcagc tgcctcaaca cagccctgtc    420
tgaggtcaag aagaacaagc tggaggatgt gccggtgctg agcaagaaga actttggcta    480
cctgcccaca caagaccctt cgggagaaga gaggatgaa caaaaacaca tcaagaacaa    540
aagaactttc tcagacgctg tgggtgggaa tggaggtaga agcatccggt acagatacca    600
atccccagca cagcccaaag gaaagctgta cccggacaag gtcaaaaacg accggggcac    660
caagttcact ctgtccctcg acgttccac taacatcatg aacatcctct tcaacattga    720
caaggccaag aatttgcgag ccaaggcagc ggccaatgct caactcatgg cacagattgg    780
gaaaaagaaa taaagcaaag gccaggcagg agggcgcccc atcgagacaa gagccccaga    840
ataagggga gggaaactga ggacgtgccc tcgaattgca aaggacggat ggtccgtttt    900
cacaggctac tccactgctg taccctctg accctctcct gcttccagcc tgtgcccaca    960
atggaggta acgtctctcc ccatatcttg tgtttgcttt ctagttccct gtggcaacag   1020
acaagttcac acagtgcccc tccttttccaa gttcctccct gatgtcccat gtctgaagag   1080
```

```
agagctctcg ggctccctct ttgttctatg ttggtctgag cctcggcaga gacacggaga    1140
agcacagctc accctcttgc taccaagtac ctcccctact tcctca                    1186
```

<210> SEQ ID NO 6
<211> LENGTH: 164
<212> TYPE: PRT
<213> ORGANISM: Rattus sp.
<220> FEATURE:
<223> OTHER INFORMATION: rat unprocessed Archipelin

<400> SEQUENCE: 6

```
Met Leu Met Pro Thr Tyr Phe Leu Leu Leu Leu Leu Leu Leu Leu Gly
 1               5                  10                  15

Gly Pro Arg Thr Ser Leu Ser His Lys Phe Tyr Asn Ala Gly Pro Ile
            20                  25                  30

Phe Ser Cys Leu Asn Thr Ala Leu Ser Glu Val Lys Lys Asn Lys Leu
        35                  40                  45

Glu Asp Val Pro Val Leu Ser Lys Lys Asn Phe Gly Tyr Leu Pro Thr
    50                  55                  60

Gln Asp Pro Ser Gly Glu Glu Asp Glu Gln Lys His Ile Lys Asn
65                  70                  75                  80

Lys Arg Thr Phe Ser Asp Ala Val Gly Gly Asn Gly Gly Arg Ser Ile
                85                  90                  95

Arg Tyr Arg Tyr Gln Ser Pro Ala Gln Pro Lys Gly Lys Leu Tyr Pro
            100                 105                 110

Asp Lys Val Lys Asn Asp Arg Gly Thr Lys Phe Thr Leu Ser Leu Asp
        115                 120                 125

Val Pro Thr Asn Ile Met Asn Ile Leu Phe Asn Ile Asp Lys Ala Lys
    130                 135                 140

Asn Leu Arg Ala Lys Ala Ala Asn Ala Gln Leu Met Ala Gln Ile
145                 150                 155                 160

Gly Lys Lys Lys
```

<210> SEQ ID NO 7
<211> LENGTH: 161
<212> TYPE: PRT
<213> ORGANISM: Homo sapiens
<220> FEATURE:
<223> OTHER INFORMATION: human unprocessed Archipelin B

<400> SEQUENCE: 7

```
Met Leu Met Pro Val His Phe Leu Leu Leu Leu Leu Leu Leu Leu Gly
 1               5                  10                  15

Gly Pro Arg Thr Gly Leu Pro His Lys Phe Tyr Lys Ala Lys Pro Ile
            20                  25                  30

Phe Ser Cys Leu Asn Thr Ala Leu Ser Glu Ala Glu Lys Gly Gln Trp
        35                  40                  45

Glu Asp Ala Ser Leu Leu Ser Lys Arg Ser Phe His Tyr Leu Arg Ser
    50                  55                  60

Arg Asp Ala Ser Ser Gly Glu Glu Glu Gly Lys Glu Lys Lys Thr
65                  70                  75                  80

Phe Pro Ile Ser Gly Ala Arg Gly Gly Ala Gly Gly Thr Arg Tyr Arg
                85                  90                  95

Tyr Val Ser Gln Ala Gln Pro Arg Gly Lys Pro Arg Gln Asp Thr Ala
            100                 105                 110

Lys Ser Pro His Arg Thr Lys Phe Thr Leu Ser Leu Asp Val Pro Thr
```

```
                115                 120                 125
Asn Ile Met Asn Leu Leu Phe Asn Ile Ala Lys Ala Lys Asn Leu Arg
    130                 135                 140

Ala Gln Ala Ala Ala Asn Ala His Leu Met Ala Gln Ile Gly Arg Lys
145                 150                 155                 160

Lys

<210> SEQ ID NO 8
<211> LENGTH: 1080
<212> TYPE: DNA
<213> ORGANISM: Homo sapiens
<220> FEATURE:
<223> OTHER INFORMATION: human Archipelin B full-length cDNA
<220> FEATURE:
<221> NAME/KEY: modified_base
<222> LOCATION: (1)..(1080)
<223> OTHER INFORMATION: n = g, a, c or t

<400> SEQUENCE: 8
cacagcccac ttaggaacaa taccggagaa gcaggagccg agaccccgga gcagccacaa      60
gttcatgggg acgtgcacgg ggccgccctc ctggccctga gctgcgccg gcctccctga    120
gcgtttcgct gcggagggaa gtccactctc ggggagagat gctgatgccg gtccacttcc    180
tgctgctcct gctgctgctc ctggggggcc caggacagg cctcccccac aagttctaca    240
aagccaagcc catcttcagc tgcctcaaca ccgccctgtc tgaggctgag aagggccagt    300
gggaggatgc atccctgctg agcaagagga gcttccacta cctgcgcagc agagacgcct    360
cttcgggaga ggaggaggag ggcaaagaga aaaagacttt ccccatctct ggggccaggg    420
gtggagccgg aggcacccgg tacagatacg tgtcccaagc acagcccagg ggaaagccac    480
gccaggacac ggccaagagt ccccaccgca ccaagttcac cctgtccctc gacgtcccca    540
ccaacatcat gaacctcctc ttcaacatcg ccaaggccaa gaacctgcgt gcccaggcgg    600
ccgccaatgc ccacctgatg gcgcaaattg gaggaagaa gtagaggcgg aggctggacg    660
ggagggcagc ggggtgngga ggggagggg aggggaggg gagggcnagg ggggagggg    720
aggggaggg tgctgtctgc tggnttgtgt tttgtgggat cagtcagttt tacaggttgc    780
tgcactgctg agcccctctg atctcttctg gcctttgacc ctgtctccct cctgctctgt    840
ctgtacacac agaagtgcag tattgtccaa ccttcccaga cacaaagcag ctaacnttcc    900
tccctgtact caacgtctcc ttcctccctc cccacagcaa gaggcaaagt tcatgcattc    960
ctcctctcca gtcttctctc tgttgacccc atgcctgaga agagagcgtt cagggctcct   1020
ctcccacaca tcaacttctg ccagggcaga agaggagct gcagcactcg ccttcctgac   1080

<210> SEQ ID NO 9
<211> LENGTH: 38
<212> TYPE: PRT
<213> ORGANISM: Homo sapiens
<220> FEATURE:
<223> OTHER INFORMATION: human Archipelin cleavage product

<400> SEQUENCE: 9

Phe Thr Leu Ser Leu Asp Val Pro Thr Asn Ile Met Asn Leu Leu Phe
  1               5                  10                  15

Asn Ile Ala Lys Ala Lys Asn Leu Arg Ala Gln Ala Ala Ala Asn Ala
             20                  25                  30

His Leu Met Ala Gln Ile
         35
```

```
<210> SEQ ID NO 10
<211> LENGTH: 40
<212> TYPE: PRT
<213> ORGANISM: Homo sapiens
<220> FEATURE:
<223> OTHER INFORMATION: human Archipelin cleavage product

<400> SEQUENCE: 10

Thr Lys Phe Thr Leu Ser Leu Asp Val Pro Thr Asn Ile Met Asn Leu
 1               5                  10                  15

Leu Phe Asn Ile Ala Lys Ala Lys Asn Leu Arg Ala Gln Ala Ala Ala
            20                  25                  30

Asn Ala His Leu Met Ala Gln Ile
        35                  40

<210> SEQ ID NO 11
<211> LENGTH: 42
<212> TYPE: PRT
<213> ORGANISM: Homo sapiens
<220> FEATURE:
<223> OTHER INFORMATION: human Archipelin cleavage product

<400> SEQUENCE: 11

Ser Pro His Arg Phe Thr Leu Ser Leu Asp Val Pro Thr Asn Ile Met
 1               5                  10                  15

Asn Leu Leu Phe Asn Ile Ala Lys Ala Lys Asn Leu Arg Ala Gln Ala
            20                  25                  30

Ala Ala Asn Ala His Leu Met Ala Gln Ile
        35                  40

<210> SEQ ID NO 12
<211> LENGTH: 49
<212> TYPE: PRT
<213> ORGANISM: Homo sapiens
<220> FEATURE:
<223> OTHER INFORMATION: human Archipelin cleavage product

<400> SEQUENCE: 12

Gln Asp Thr Ala Lys Ser Pro His Arg Thr Lys Phe Thr Leu Ser Leu
 1               5                  10                  15

Asp Val Pro Thr Asn Ile Met Asn Leu Leu Phe Asn Ile Ala Lys Ala
            20                  25                  30

Lys Asn Leu Arg Ala Gln Ala Ala Ala Asn Ala His Leu Met Ala Gln
        35                  40                  45

Ile

<210> SEQ ID NO 13
<211> LENGTH: 51
<212> TYPE: PRT
<213> ORGANISM: Homo sapiens
<220> FEATURE:
<223> OTHER INFORMATION: human Archipelin cleavage product

<400> SEQUENCE: 13

Pro Arg Gln Asp Thr Ala Lys Ser Pro His Arg Thr Lys Phe Thr Leu
 1               5                  10                  15

Ser Leu Asp Val Pro Thr Asn Ile Met Asn Leu Leu Phe Asn Ile Ala
            20                  25                  30

Lys Ala Lys Asn Leu Arg Ala Gln Ala Ala Ala Asn Ala His Leu Met
        35                  40                  45

Ala Gln Ile
```

-continued

```
<210> SEQ ID NO 14
<211> LENGTH: 53
<212> TYPE: PRT
<213> ORGANISM: Homo sapiens
<220> FEATURE:
<223> OTHER INFORMATION: human Archipelin cleavage product

<400> SEQUENCE: 14
```

Gly Lys Pro Arg Gln Asp Thr Ala Lys Ser Pro His Arg Thr Lys Phe
 1               5                  10                  15

Thr Leu Ser Leu Asp Val Pro Thr Asn Ile Met Asn Leu Leu Phe Asn
            20                  25                  30

Ile Ala Lys Ala Lys Asn Leu Arg Ala Gln Ala Ala Ala Asn Ala His
        35                  40                  45

Leu Met Ala Gln Ile
    50

```
<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence:reverse
      amplification primer for human Archipelin

<400> SEQUENCE: 15
```
gcgatgttga agaagaagtt c                                           21

```
<210> SEQ ID NO 16
<211> LENGTH: 16
<212> TYPE: DNA
<213> ORGANISM: Artificial Sequence
<220> FEATURE:
<223> OTHER INFORMATION: Description of Artificial Sequence:forward
      amplification primer for human Archipelin

<400> SEQUENCE: 16
```
atcgccaagg ccaaga                                                 16

```
<210> SEQ ID NO 17
<211> LENGTH: 32
<212> TYPE: PRT
<213> ORGANISM: Artificial Sequence
<220> FEATURE:
<223> OTHER INFORMATION: Description of Artificial Sequence:tobacco
      hornworm diuretic hormone 1 precursor
      corticotropin-releasing factor (CRF) family
      peptide

<400> SEQUENCE: 17
```

Pro Ser Leu Ser Ile Asp Leu Pro Met Ser Val Leu Arg Gln Lys Leu
 1               5                  10                  15

Ser Leu Glu Lys Glu Arg Lys Val His Ala Leu Arg Ala Ala Ala Asn
            20                  25                  30

```
<210> SEQ ID NO 18
<211> LENGTH: 32
<212> TYPE: PRT
<213> ORGANISM: Artificial Sequence
<220> FEATURE:
<223> OTHER INFORMATION: Description of Artificial Sequence:tobacco
      hornworm diuretic hormone 2
      corticotropin-releasing factor (CRF) family
      peptide
```

```
<220> FEATURE:
<221> NAME/KEY: MOD_RES
<222> LOCATION: (1)..(32)
<223> OTHER INFORMATION: Xaa = any amino acid

<400> SEQUENCE: 18

Xaa Ser Phe Ser Val Asn Pro Ala Val Asp Ile Leu Gln His Arg Tyr
 1               5                  10                  15

Met Glu Lys Val Ala Gln Asn Asn Arg Asn Phe Leu Asn Arg Val Xaa
            20                  25                  30

<210> SEQ ID NO 19
<211> LENGTH: 32
<212> TYPE: PRT
<213> ORGANISM: Artificial Sequence
<220> FEATURE:
<223> OTHER INFORMATION: Description of Artificial Sequence:
      house cricket diuretic hormone corticotropin-releasing factor
      (CRF) family peptide

<400> SEQUENCE: 19

Gln Ser Leu Ser Ile Val Ala Pro Leu Asp Val Leu Arg Gln Arg Leu
 1               5                  10                  15

Met Asn Glu Leu Asn Arg Arg Arg Met Arg Glu Leu Gln Gly Ser Arg
            20                  25                  30

<210> SEQ ID NO 20
<211> LENGTH: 32
<212> TYPE: PRT
<213> ORGANISM: Artificial Sequence
<220> FEATURE:
<223> OTHER INFORMATION: Description of Artificial Sequence:sauvage's
      leaf frog sauvagine corticotropin-releasing factor
      (CRF) family peptide

<400> SEQUENCE: 20

Pro Pro Ile Ser Ile Asp Leu Ser Leu Glu Leu Leu Arg Lys Met Ile
 1               5                  10                  15

Glu Ile Glu Lys Gln Glu Lys Glu Lys Gln Gln Ala Ala Asn Asn Arg
            20                  25                  30

<210> SEQ ID NO 21
<211> LENGTH: 32
<212> TYPE: PRT
<213> ORGANISM: Artificial Sequence
<220> FEATURE:
<223> OTHER INFORMATION: Description of Artificial Sequence:
      white sucker corticoliberin 1 precursor, human pig and rat
      corticoliberin precursor corticotropin-releasing factor (CRF)
      family peptide

<400> SEQUENCE: 21

Pro Pro Ile Ser Leu Asp Leu Thr Phe His Leu Leu Arg Glu Val Leu
 1               5                  10                  15

Glu Met Ala Arg Ala Glu Gln Leu Ala Gln Gln Ala His Ser Asn Arg
            20                  25                  30

<210> SEQ ID NO 22
<211> LENGTH: 32
<212> TYPE: PRT
<213> ORGANISM: Artificial Sequence
<220> FEATURE:
<223> OTHER INFORMATION: Description of Artificial Sequence:white sucker
      corticoliberin 2 precursor corticotropin-releasing
      factor (CRF) family peptide

<400> SEQUENCE: 22
```

```
Pro Pro Ile Ser Leu Asp Leu Thr Phe His Leu Leu Arg Glu Val Leu
 1               5                  10                  15

Glu Met Ala Arg Ala Glu Gln Leu Val Gln Gln Ala His Ser Asn Arg
                20                  25                  30

<210> SEQ ID NO 23
<211> LENGTH: 32
<212> TYPE: PRT
<213> ORGANISM: Artificial Sequence
<220> FEATURE:
<223> OTHER INFORMATION: Description of Artificial Sequence:sheep
      corticoliberin precursor corticotropin-releasing
      factor (CRF) family peptide

<400> SEQUENCE: 23

Pro Pro Ile Ser Leu Asp Leu Thr Phe His Leu Leu Arg Glu Val Leu
 1               5                  10                  15

Glu Met Thr Lys Ala Asp Gln Leu Ala Gln Gln Ala His Ser Asn Arg
                20                  25                  30

<210> SEQ ID NO 24
<211> LENGTH: 32
<212> TYPE: PRT
<213> ORGANISM: Artificial Sequence
<220> FEATURE:
<223> OTHER INFORMATION: Description of Artificial Sequence:xenopus
      corticoliberin precursor corticotropin-releasing
      factor (CRF) family peptide

<400> SEQUENCE: 24

Pro Pro Ile Ser Leu Asp Leu Thr Phe His Leu Leu Arg Glu Val Leu
 1               5                  10                  15

Glu Met Ala Arg Ala Glu Gln Ile Ala Gln Gln Ala His Ser Asn Arg
                20                  25                  30

<210> SEQ ID NO 25
<211> LENGTH: 32
<212> TYPE: PRT
<213> ORGANISM: Artificial Sequence
<220> FEATURE:
<223> OTHER INFORMATION: Description of Artificial Sequence:
      locust diuretic hormone corticotropin-releasing factor (CRF)
      family peptide

<400> SEQUENCE: 25

Pro Ser Leu Ser Ile Val Asn Pro Met Asp Val Leu Arg Gln Arg Leu
 1               5                  10                  15

Leu Leu Glu Ile Ala Arg Arg Arg Leu Arg Asp Ala Glu Glu Gln Ile
                20                  25                  30

<210> SEQ ID NO 26
<211> LENGTH: 32
<212> TYPE: PRT
<213> ORGANISM: Artificial Sequence
<220> FEATURE:
<223> OTHER INFORMATION: Description of Artificial Sequence:stable fly
      diuretic hormone corticotropin-releasing factor
      (CRF) family peptide

<400> SEQUENCE: 26

Pro Ser Leu Ser Ile Val Asn Pro Leu Asp Val Leu Arg Gln Arg Leu
 1               5                  10                  15

Leu Leu Glu Ile Ala Arg Arg Gln Met Lys Glu Asn Thr Arg Gln Val
                20                  25                  30
```

<210> SEQ ID NO 27
<211> LENGTH: 32
<212> TYPE: PRT
<213> ORGANISM: Artificial Sequence
<220> FEATURE:
<223> OTHER INFORMATION: Description of Artificial Sequence:cockroach
      diuretic hormone corticotropin-releasing factor
      (CRF) family peptide

<400> SEQUENCE: 27

Pro Ser Leu Ser Ile Val Asn Pro Leu Asp Val Leu Arg Gln Arg Leu
 1               5                  10                  15

Leu Leu Glu Ile Ala Arg Arg Arg Met Arg Gln Ser Gln Asp Gln Ile
            20                  25                  30

<210> SEQ ID NO 28
<211> LENGTH: 32
<212> TYPE: PRT
<213> ORGANISM: Artificial Sequence
<220> FEATURE:
<223> OTHER INFORMATION: Description of Artificial Sequence:white sucker
      urotensin I corticotropin-releasing factor (CRF)
      family peptide

<400> SEQUENCE: 28

Pro Pro Ile Ser Ile Asp Leu Thr Phe His Leu Leu Arg Asn Met Ile
 1               5                  10                  15

Glu Met Ala Arg Ile Glu Asn Glu Arg Glu Gln Ala Gly Leu Asn Arg
            20                  25                  30

<210> SEQ ID NO 29
<211> LENGTH: 32
<212> TYPE: PRT
<213> ORGANISM: Artificial Sequence
<220> FEATURE:
<223> OTHER INFORMATION: Description of Artificial Sequence:common carp
      urotensin I precursor corticotropin-releasing
      factor (CRF) family peptide

<400> SEQUENCE: 29

Pro Pro Ile Ser Ile Asp Leu Thr Phe His Leu Leu Arg Asn Met Ile
 1               5                  10                  15

Glu Met Ala Arg Asn Glu Asn Gln Arg Glu Gln Ala Gly Leu Asn Arg
            20                  25                  30

<210> SEQ ID NO 30
<211> LENGTH: 32
<212> TYPE: PRT
<213> ORGANISM: Artificial Sequence
<220> FEATURE:
<223> OTHER INFORMATION: Description of Artificial Sequence:
      human urocortin precursor corticotropin-releasing factor (CRF)
      family peptide

<400> SEQUENCE: 30

Pro Ser Leu Ser Ile Asp Leu Thr Phe His Leu Leu Arg Thr Leu Leu
 1               5                  10                  15

Glu Leu Ala Arg Thr Gln Ser Gln Arg Glu Arg Ala Glu Gln Asn Arg
            20                  25                  30

<210> SEQ ID NO 31
<211> LENGTH: 32
<212> TYPE: PRT
<213> ORGANISM: Artificial Sequence
<220> FEATURE:
<223> OTHER INFORMATION: Description of Artificial Sequence:rat and mouse urocortin precursor corticotropin-releasing factor
(CRF) family peptide

<400> SEQUENCE: 31

Pro Pro Leu Ser Ile Asp Leu Thr Phe His Leu Leu Arg Thr Leu Leu
 1               5                  10                  15

Glu Leu Ala Arg Thr Gln Ser Gln Arg Glu Arg Ala Glu Gln Asn Arg
            20                  25                  30

<210> SEQ ID NO 32
<211> LENGTH: 32
<212> TYPE: PRT
<213> ORGANISM: Artificial Sequence
<220> FEATURE:
<223> OTHER INFORMATION: Description of Artificial Sequence:pufferfish
      urocortin precursor corticotropin-releasing factor
      (CRF) family peptide

<400> SEQUENCE: 32

Leu Thr Leu Ser Leu Asp Val Pro Thr Asn Ile Met Asn Val Leu Phe
 1               5                  10                  15

Asp Val Ala Lys Ala Lys Asn Leu Arg Ala Lys Ala Ala Glu Asn Ala
            20                  25                  30

<210> SEQ ID NO 33
<211> LENGTH: 32
<212> TYPE: PRT
<213> ORGANISM: Artificial Sequence
<220> FEATURE:
<223> OTHER INFORMATION: Description of Artificial Sequence:human
      Archipelin peptide

<400> SEQUENCE: 33

Phe Thr Leu Ser Leu Asp Val Pro Thr Asn Ile Met Asn Leu Leu Phe
 1               5                  10                  15

Asn Ile Ala Lys Ala Lys Asn Leu Arg Ala Gln Ala Ala Ala Asn Ala
            20                  25                  30

<210> SEQ ID NO 34
<211> LENGTH: 32
<212> TYPE: PRT
<213> ORGANISM: Artificial Sequence
<220> FEATURE:
<223> OTHER INFORMATION: Description of Artificial Sequence:
      rat and mouse Archipelin peptide

<400> SEQUENCE: 34

Phe Thr Leu Ser Leu Asp Val Pro Thr Asn Ile Met Asn Ile Leu Phe
 1               5                  10                  15

Asn Ile Asp Lys Ala Lys Asn Leu Arg Ala Lys Ala Ala Ala Asn Ala
            20                  25                  30

<210> SEQ ID NO 35
<211> LENGTH: 38
<212> TYPE: PRT
<213> ORGANISM: Homo sapiens
<220> FEATURE:
<221> NAME/KEY: MOD_RES
<222> LOCATION: (38)
<223> OTHER INFORMATION: Xaa = isoleucinamide

<400> SEQUENCE: 35

Phe Thr Leu Ser Leu Asp Val Pro Thr Asn Ile Met Asn Leu Leu Phe
 1               5                  10                  15

Asn Ile Ala Lys Ala Lys Asn Leu Arg Ala Gln Ala Ala Ala Asn Ala

His Leu Met Ala Gln Xaa
         35

<210> SEQ ID NO 36
<211> LENGTH: 40
<212> TYPE: PRT
<213> ORGANISM: Homo sapiens
<220> FEATURE:
<221> NAME/KEY: MOD_RES
<222> LOCATION: (40)
<223> OTHER INFORMATION: Xaa = isoleucinamide

<400> SEQUENCE: 36

Thr Lys Phe Thr Leu Ser Leu Asp Val Pro Thr Asn Ile Met Asn Leu
 1               5                  10                  15

Leu Phe Asn Ile Ala Lys Ala Lys Asn Leu Arg Ala Gln Ala Ala Ala
            20                  25                  30

Asn Ala His Leu Met Ala Gln Xaa
        35                  40

<210> SEQ ID NO 37
<211> LENGTH: 44
<212> TYPE: PRT
<213> ORGANISM: Homo sapiens
<220> FEATURE:
<221> NAME/KEY: MOD_RES
<222> LOCATION: (44)
<223> OTHER INFORMATION: Xaa = isoleucinamide

<400> SEQUENCE: 37

Ser Pro His Arg Thr Lys Phe Thr Leu Ser Leu Asp Val Pro Thr Asn
 1               5                  10                  15

Ile Met Asn Leu Leu Phe Asn Ile Ala Lys Ala Lys Asn Leu Arg Ala
            20                  25                  30

Gln Ala Ala Ala Asn Ala His Leu Met Ala Gln Xaa
        35                  40

<210> SEQ ID NO 38
<211> LENGTH: 49
<212> TYPE: PRT
<213> ORGANISM: Homo sapiens
<220> FEATURE:
<221> NAME/KEY: MOD_RES
<222> LOCATION: (49)
<223> OTHER INFORMATION: Xaa = isoleucinamide

<400> SEQUENCE: 38

Gln Asp Thr Ala Lys Ser Pro His Arg Thr Lys Phe Thr Leu Ser Leu
 1               5                  10                  15

Asp Val Pro Thr Asn Ile Met Asn Leu Leu Phe Asn Ile Ala Lys Ala
            20                  25                  30

Lys Asn Leu Arg Ala Gln Ala Ala Ala Asn Ala His Leu Met Ala Gln
        35                  40                  45

Xaa

<210> SEQ ID NO 39
<211> LENGTH: 51
<212> TYPE: PRT
<213> ORGANISM: Homo sapiens
<220> FEATURE:
<221> NAME/KEY: MOD_RES
<222> LOCATION: (51)
<223> OTHER INFORMATION: Xaa = isoleucinamide -continued

<400> SEQUENCE: 39

Pro Arg Gln Asp Thr Ala Lys Ser Pro His Arg Thr Lys Phe Thr Leu
1               5                   10                  15

Ser Leu Asp Val Pro Thr Asn Ile Met Asn Leu Leu Phe Asn Ile Ala
            20                  25                  30

Lys Ala Lys Asn Leu Arg Ala Gln Ala Ala Asn Ala His Leu Met
        35                  40                  45

Ala Gln Xaa
        50

<210> SEQ ID NO 40
<211> LENGTH: 53
<212> TYPE: PRT
<213> ORGANISM: Homo sapiens
<220> FEATURE:
<221> NAME/KEY: MOD_RES
<222> LOCATION: (53)
<223> OTHER INFORMATION: Xaa = isoleucinamide

<400> SEQUENCE: 40

Gly Lys Pro Arg Gln Asp Thr Ala Lys Ser Pro His Arg Thr Lys Phe
1               5                   10                  15

Thr Leu Ser Leu Asp Val Pro Thr Asn Ile Met Asn Leu Leu Phe Asn
            20                  25                  30

Ile Ala Lys Ala Lys Asn Leu Arg Ala Gln Ala Ala Ala Asn Ala His
        35                  40                  45

Leu Met Ala Gln Xaa
        50

<210> SEQ ID NO 41
<211> LENGTH: 40
<212> TYPE: PRT
<213> ORGANISM: Mus sp. and Rattus sp.
<220> FEATURE:
<221> NAME/KEY: MOD_RES
<222> LOCATION: (40)
<223> OTHER INFORMATION: Xaa = isoleucinamide

<400> SEQUENCE: 41

Thr Lys Phe Thr Leu Ser Leu Asp Val Pro Thr Asn Ile Met Asn Ile
1               5                   10                  15

Leu Phe Asn Ile Asp Lys Ala Lys Asn Leu Arg Ala Lys Ala Ala Ala
            20                  25                  30

Asn Ala Gln Leu Met Ala Gln Xaa
        35                  40

<210> SEQ ID NO 42
<211> LENGTH: 41
<212> TYPE: PRT
<213> ORGANISM: Mus sp. and Rattus sp.
<220> FEATURE:
<221> NAME/KEY: MOD_RES
<222> LOCATION: (41)
<223> OTHER INFORMATION: Xaa = isoleucinamide

<400> SEQUENCE: 42

Gly Thr Lys Phe Thr Leu Ser Leu Asp Val Pro Thr Asn Ile Met Asn
1               5                   10                  15

Ile Leu Phe Asn Ile Asp Lys Ala Lys Asn Leu Arg Ala Lys Ala Ala
            20                  25                  30

Ala Asn Ala Gln Leu Met Ala Gln Xaa

```
<210> SEQ ID NO 43
<211> LENGTH: 44
<212> TYPE: PRT
<213> ORGANISM: Mus sp.
<220> FEATURE:
<221> NAME/KEY: MOD_RES
<222> LOCATION: (44)
<223> OTHER INFORMATION: Xaa = isoleucinamide

<400> SEQUENCE: 43

Ser Asp Arg Gly Thr Lys Phe Thr Leu Ser Leu Asp Val Pro Thr Asn
 1               5                  10                  15

Ile Met Asn Ile Leu Phe Asn Ile Asp Lys Ala Lys Asn Leu Arg Ala
                20                  25                  30

Lys Ala Ala Asn Ala Gln Leu Met Ala Gln Xaa
            35                  40

<210> SEQ ID NO 44
<211> LENGTH: 46
<212> TYPE: PRT
<213> ORGANISM: Mus sp.
<220> FEATURE:
<221> NAME/KEY: MOD_RES
<222> LOCATION: (46)
<223> OTHER INFORMATION: Xaa = isoleucinamide

<400> SEQUENCE: 44

Pro Lys Ser Asp Arg Gly Thr Lys Phe Thr Leu Ser Leu Asp Val Pro
 1               5                  10                  15

Thr Asn Ile Met Asn Ile Leu Phe Asn Ile Asp Lys Ala Lys Asn Leu
                20                  25                  30

Arg Ala Lys Ala Ala Ala Asn Ala Gln Leu Met Ala Gln Xaa
            35                  40                  45

<210> SEQ ID NO 45
<211> LENGTH: 51
<212> TYPE: PRT
<213> ORGANISM: Mus sp. and Rattus sp.
<220> FEATURE:
<221> NAME/KEY: MOD_RES
<222> LOCATION: (51)
<223> OTHER INFORMATION: Xaa = isoleucinamide

<400> SEQUENCE: 45

Leu Tyr Pro Asp Lys Pro Lys Ser Asp Arg Gly Thr Lys Phe Thr Leu
 1               5                  10                  15

Ser Leu Asp Val Pro Thr Asn Ile Met Asn Ile Leu Phe Asn Ile Asp
                20                  25                  30

Lys Ala Lys Asn Leu Arg Ala Lys Ala Ala Asn Ala Gln Leu Met
            35                  40                  45

Ala Gln Xaa
        50

<210> SEQ ID NO 46
<211> LENGTH: 44
<212> TYPE: PRT
<213> ORGANISM: Rattus sp.
<220> FEATURE:
<221> NAME/KEY: MOD_RES
<222> LOCATION: (44)
<223> OTHER INFORMATION: Xaa = isoleucinamide

<400> SEQUENCE: 46
```

```
Asn Asp Arg Gly Thr Lys Phe Thr Leu Ser Leu Asp Val Pro Thr Asn
 1               5                  10                  15

Ile Met Asn Ile Leu Phe Asn Ile Asp Lys Ala Lys Asn Leu Arg Ala
                20                  25                  30

Lys Ala Ala Ala Asn Ala Gln Leu Met Ala Gln Xaa
        35                  40
```

<210> SEQ ID NO 47
<211> LENGTH: 46
<212> TYPE: PRT
<213> ORGANISM: Rattus sp.
<220> FEATURE:
<221> NAME/KEY: MOD_RES
<222> LOCATION: (46)
<223> OTHER INFORMATION: Xaa = isoleucinamide

<400> SEQUENCE: 47

```
Val Lys Asn Asp Arg Gly Thr Lys Phe Thr Leu Ser Leu Asp Val Pro
 1               5                  10                  15

Thr Asn Ile Met Asn Ile Leu Phe Asn Ile Asp Lys Ala Lys Asn Leu
                20                  25                  30

Arg Ala Lys Ala Ala Ala Asn Ala Gln Leu Met Ala Gln Xaa
        35                  40                  45
```

<210> SEQ ID NO 48
<211> LENGTH: 52
<212> TYPE: PRT
<213> ORGANISM: Rattus sp.
<220> FEATURE:
<221> NAME/KEY: MOD_RES
<222> LOCATION: (52)
<223> OTHER INFORMATION: Xaa = isoleucinamide

<400> SEQUENCE: 48

```
Gly Leu Tyr Pro Asp Lys Val Lys Asn Asp Arg Gly Thr Lys Phe Thr
 1               5                  10                  15

Leu Ser Leu Asp Val Pro Thr Asn Ile Met Asn Ile Leu Phe Asn Ile
                20                  25                  30

Asp Lys Ala Lys Asn Leu Arg Ala Lys Ala Ala Ala Asn Ala Gln Leu
        35                  40                  45

Met Ala Gln Xaa
     50
```

<210> SEQ ID NO 49
<211> LENGTH: 11
<212> TYPE: PRT
<213> ORGANISM: Rattus sp.
<220> FEATURE:
<223> OTHER INFORMATION: rat Archipelin peptide from rat serum

<400> SEQUENCE: 49

```
Ala Ala Ala Asn Ala Gln Leu Met Ala Gln Ile
 1               5                  10
```

<210> SEQ ID NO 50
<211> LENGTH: 13
<212> TYPE: PRT
<213> ORGANISM: Rattus sp.
<220> FEATURE:
<223> OTHER INFORMATION: rat Archipelin peptide from rat serum

<400> SEQUENCE: 50

```
Ala Lys Ala Ala Ala Asn Ala Gln Leu Met Ala Gln Ile
 1               5                  10
```

```
<210> SEQ ID NO 51
<211> LENGTH: 22
<212> TYPE: PRT
<213> ORGANISM: Rattus sp.
<220> FEATURE:
<223> OTHER INFORMATION: rat Archipelin peptide from rat serum

<400> SEQUENCE: 51

Phe Thr Leu Ser Leu Asp Val Pro Thr Asn Ile Met Asn Ile Leu Phe
 1               5                  10                  15

Asn Ile Asp Lys Ala Lys
            20

<210> SEQ ID NO 52
<211> LENGTH: 20
<212> TYPE: PRT
<213> ORGANISM: Rattus sp.
<220> FEATURE:
<223> OTHER INFORMATION: rat Archipelin peptide from rat serum

<400> SEQUENCE: 52

Phe Thr Leu Ser Leu Asp Val Pro Thr Asn Ile Met Asn Ile Leu Phe
 1               5                  10                  15

Asn Ile Asp Lys
            20

<210> SEQ ID NO 53
<211> LENGTH: 200
<212> TYPE: PRT
<213> ORGANISM: Artificial Sequence
<220> FEATURE:
<223> OTHER INFORMATION: Description of Artificial Sequence:poly Gly
      flexible linker
<220> FEATURE:
<221> NAME/KEY: MOD_RES
<222> LOCATION: (6)...(200)
<223> OTHER INFORMATION: Gly at positions 6-200 may be present or
      absent

<400> SEQUENCE: 53

Gly Gly Gly Gly Gly Gly Gly Gly Gly Gly Gly Gly Gly Gly Gly
 1               5                  10                  15

Gly Gly Gly Gly Gly Gly Gly Gly Gly Gly Gly Gly Gly Gly Gly
            20                  25                  30

Gly Gly Gly Gly Gly Gly Gly Gly Gly Gly Gly Gly Gly Gly Gly
        35                  40                  45

Gly Gly Gly Gly Gly Gly Gly Gly Gly Gly Gly Gly Gly Gly Gly
    50                  55                  60

Gly Gly Gly Gly Gly Gly Gly Gly Gly Gly Gly Gly Gly Gly Gly
 65                  70                  75                  80

Gly Gly Gly Gly Gly Gly Gly Gly Gly Gly Gly Gly Gly Gly Gly
            85                  90                  95

Gly Gly Gly Gly Gly Gly Gly Gly Gly Gly Gly Gly Gly Gly Gly
            100                 105                 110

Gly Gly Gly Gly Gly Gly Gly Gly Gly Gly Gly Gly Gly Gly Gly
            115                 120                 125

Gly Gly Gly Gly Gly Gly Gly Gly Gly Gly Gly Gly Gly Gly Gly
            130                 135                 140

Gly Gly Gly Gly Gly Gly Gly Gly Gly Gly Gly Gly Gly Gly Gly
145                 150                 155                 160

Gly Gly Gly Gly Gly Gly Gly Gly Gly Gly Gly Gly Gly Gly Gly
            165                 170                 175
```

```
Gly Gly Gly Gly Gly Gly Gly Gly Gly Gly Gly Gly Gly
            180                 185                 190
Gly Gly Gly Gly Gly Gly Gly Gly
        195                 200
```

<210> SEQ ID NO 54
<211> LENGTH: 14
<212> TYPE: PRT
<213> ORGANISM: Artificial Sequence
<220> FEATURE:
<223> OTHER INFORMATION: Description of Artificial Sequence:rat and mouse
      Archipelin peptide used to develop antisera

<400> SEQUENCE: 54

```
Cys Leu Phe Asn Ile Asp Lys Ala Lys Asn Leu Arg Ala Lys
 1               5                  10
```

<210> SEQ ID NO 55
<211> LENGTH: 40
<212> TYPE: PRT
<213> ORGANISM: Homo sapiens
<220> FEATURE:
<223> OTHER INFORMATION: major serum form of human Archipelin peptide

<400> SEQUENCE: 55

```
Thr Lys Phe Thr Leu Ser Leu Asp Val Pro Thr Asn Ile Met Asn Leu
 1               5                  10                  15
Leu Phe Asn Ile Ala Lys Ala Lys Asn Leu Arg Ala Gln Ala Ala Ala
            20                  25                  30
Asn Ala His Leu Met Ala Gln Ile
        35                  40
```

<210> SEQ ID NO 56
<211> LENGTH: 41
<212> TYPE: PRT
<213> ORGANISM: Homo sapiens
<220> FEATURE:
<223> OTHER INFORMATION: major serum form of human Archipelin peptide

<400> SEQUENCE: 56

```
Arg Thr Lys Phe Thr Leu Ser Leu Asp Val Pro Thr Asn Ile Met Asn
 1               5                  10                  15
Leu Leu Phe Asn Ile Ala Lys Ala Lys Asn Leu Arg Ala Gln Ala Ala
            20                  25                  30
Ala Asn Ala His Leu Met Ala Gln Ile
        35                  40
```

<210> SEQ ID NO 57
<211> LENGTH: 38
<212> TYPE: PRT
<213> ORGANISM: Rattus sp.
<220> FEATURE:
<223> OTHER INFORMATION: major serum form of rat Archipelin peptide

<400> SEQUENCE: 57

```
Phe Thr Leu Ser Leu Asp Val Pro Thr Asn Ile Met Asn Ile Leu Phe
 1               5                  10                  15
Asn Ile Asp Lys Ala Lys Asn Leu Arg Ala Lys Ala Ala Ala Asn Ala
            20                  25                  30
Gln Leu Met Ala Gln Ile
        35
```